(12) United States Patent
Ohsawa et al.

(10) Patent No.: US 8,173,354 B2
(45) Date of Patent: May 8, 2012

(54) SULFONIUM SALT, RESIST COMPOSITION, AND PATTERNING PROCESS

(75) Inventors: Youichi Ohsawa, Joetsu (JP); Masaki Ohashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 126 days.

(21) Appl. No.: 12/831,621

(22) Filed: Jul. 7, 2010

(65) Prior Publication Data

US 2011/0008735 A1 Jan. 13, 2011

(30) Foreign Application Priority Data

Jul. 8, 2009 (JP) ................................ 2009-161322

(51) Int. Cl.
G03F 7/004 (2006.01)
G03F 7/30 (2006.01)
C07C 309/06 (2006.01)
C07C 309/25 (2006.01)
C07C 309/28 (2006.01)

(52) U.S. Cl. ...................... 430/270.1; 430/326; 430/330; 430/907; 430/910; 430/921; 562/41; 562/75; 562/83; 562/100; 568/34

(58) Field of Classification Search .............. 430/270.1, 430/326, 330, 907, 910, 921; 562/41, 75, 562/83, 100; 568/34
See application file for complete search history.

(56) References Cited

U.S. PATENT DOCUMENTS

| | | | |
|---|---|---|---|
| 5,650,483 A | 7/1997 | Malik et al. | |
| 6,136,502 A | 10/2000 | Satoshi et al. | |
| 6,312,867 B1 | 11/2001 | Kinsho et al. | |
| 6,641,975 B2 | 11/2003 | Takeda et al. | |
| 6,653,044 B2 | 11/2003 | Takeda et al. | |
| 6,746,817 B2 | 6/2004 | Takeda et al. | |
| 6,830,866 B2 | 12/2004 | Kobayashi et al. | |
| 6,835,804 B2 | 12/2004 | Takeda et al. | |
| 6,949,323 B2 | 9/2005 | Takeda et al. | |
| 7,267,923 B2 | 9/2007 | Takeda et al. | |
| 7,501,223 B2 | 3/2009 | Takeda et al. | |
| 7,537,880 B2 | 5/2009 | Harada et al. | |
| 7,642,368 B2* | 1/2010 | Sumino et al. | 558/412 |
| 7,670,751 B2 | 3/2010 | Ohashi et al. | |
| 7,745,097 B2* | 6/2010 | Hada et al. | 430/270.1 |
| 2004/0260031 A1 | 12/2004 | Takeda et al. | |
| 2007/0083060 A1* | 4/2007 | Sumino et al. | 558/412 |
| 2007/0231738 A1 | 10/2007 | Kaneko et al. | |
| 2007/0298352 A1* | 12/2007 | Kobayashi et al. | 430/302 |
| 2008/0090172 A1 | 4/2008 | Hatakeyama et al. | |
| 2008/0090173 A1 | 4/2008 | Harada et al. | |
| 2008/0096128 A1 | 4/2008 | Takeda et al. | |
| 2008/0318160 A1 | 12/2008 | Ohsawa et al. | |
| 2009/0047598 A1 | 2/2009 | Yamashita et al. | |
| 2010/0035185 A1 | 2/2010 | Hagiwara et al. | |
| 2011/0152540 A1* | 6/2011 | Nakayashiki et al. | 549/43 |

FOREIGN PATENT DOCUMENTS

| | | |
|---|---|---|
| JP | 11-190904 A | 7/1999 |
| JP | 2000-336121 A | 12/2000 |
| JP | 2001-272785 A | 10/2001 |
| JP | 2002-62652 A | 2/2002 |
| JP | 2002-202610 A | 7/2002 |
| JP | 2002-234910 A | 8/2002 |
| JP | 2003-66612 A | 3/2003 |
| JP | 2003-107706 A | 4/2003 |
| JP | 2003-131384 A | 5/2003 |
| JP | 2005-8766 A | 1/2005 |
| JP | 2007-145797 A | 6/2007 |
| JP | 3981830 B2 | 9/2007 |
| JP | 2007-297590 A | 11/2007 |
| JP | 2008-88343 A | 4/2008 |
| JP | 2008-95009 A | 4/2008 |
| JP | 2008-102383 A | 5/2008 |
| JP | 2008-111103 A | 5/2008 |
| JP | 2008-122932 A | 5/2008 |
| JP | 2009-7327 A | 1/2009 |
| JP | 2009-37057 A | 2/2009 |
| JP | 2009-80474 A | 4/2009 |
| KR | 10-2009-0013727 A | 2/2009 |

OTHER PUBLICATIONS

Arimitsu et al., "Effect of Phenolic Hydroxyl Residues on the Improvement of Acid-Proliferation-Type Photoimaging Materials", Journal of Photopolymer Science and Technology, 1996, vol. 9, No. 1, pp. 29-30.
Arimitsu et al., "Sensitivity Enhancement of Chemical-Amplification-Type Photoimaging Materials by Acetoacetic Acid Derivatives", Journal of Photopolymer Science and Technology, 1995, vol. 8, No. 1, pp. 43-44.
Dammel et al., "193 nm Immersion Lithography—Taking the Plunge", Journal of Photopolymer Science and Technology, 2004, vol. 17, No. 4, pp. 587-601.
Kudo et al., "Enhancement of the Sensitivity of Chemical-Amplification-Type Photoimaging Materials by β-Tosyloxyketone Acetals", Journal of Photopolymer Science and Technology, 1995, vol. 8, No. 1, pp. 45-46.

* cited by examiner

*Primary Examiner* — John Chu
(74) *Attorney, Agent, or Firm* — Birch, Stewart, Kolasch & Birch, LLP

(57) ABSTRACT

A sulfonium salt having a triphenylsulfonium cation and a sulfite anion within the molecule is best suited as a photoacid generator in chemically amplified resist compositions. Upon exposure to high-energy radiation, the sulfonium salt generates a sulfonic acid, which facilitates efficient scission of acid labile groups in chemically amplified positive resist compositions. Because of substantial non-volatility under high vacuum conditions in the EB or EUV lithography, the risk of the exposure tool being contaminated is minimized.

8 Claims, 4 Drawing Sheets

SULFONIUM SALT, RESIST COMPOSITION, AND PATTERNING PROCESS

CROSS-REFERENCE TO RELATED APPLICATION

This non-provisional application claims priority under 35 U.S.C. §119(a) on Patent Application No. 2009-161322 filed in Japan on Jul. 8, 2009, the entire contents of which are hereby incorporated by reference.

TECHNICAL FIELD

This invention relates to (1) a sulfonium salt having a sulfo group in the molecule, (2) a resist composition comprising the sulfonium salt, and (4) a patterning process using the resist composition.

BACKGROUND ART

While a number of recent efforts are being made to achieve a finer pattern rule in the drive for higher integration and operating speeds in LSI devices, deep UV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer and that allows the projection lens to be designed to a numerical aperture (NA) of 1.0 or higher and achieves a higher resolution. See Journal of Photopolymer Science and Technology, Vol. 17, No. 4, p 587 (2004).

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Studies have also been made on photoacid generators. In prior art chemically amplified resist compositions for the lithography using KrF excimer laser, photoacid generators capable of generating alkane- or arene-sulfonic acids are used. However, the use of these photoacid generators in chemically amplified resist compositions for ArF lithography encounters several drawbacks including an insufficient acid strength to scissor acid labile groups on the resin, a failure of resolution, and a low sensitivity. Thus these photoacid generators are not suited for the fabrication of microelectronic devices.

For the above reason, sulfonium salts comprising a triphenylsulfonium cation and a perfluoroalkanesulfonic acid anion are generally used as the photoacid generator in ArF chemically amplified resist compositions. Among perfluoroalkanesulfonic acids, perfluorooctanesulfonic acid (PFOS) is difficult to apply to resist materials because of its risks of difficult degradation, biological concentration and toxicity. Although photoacid generators capable of generating perfluorobutanesulfonic acid are used in the existing resist materials, it is still difficult to provide a high resolution because the acid generated therefrom are highly diffusible.

The lithography techniques which are considered promising next to the ArF lithography include electron beam (EB) lithography, $F_2$ lithography, extreme ultraviolet (EUV) lithography, and x-ray lithography. In these techniques, exposure must be done in vacuum or reduced pressure, which allows the sulfonic acid generated during exposure to volatilize, failing to form a satisfactory pattern profile. Volatile sulfonic acids and volatile photolysis products of sulfonium cations (e.g., phenylsulfides) become so-called outgases which can damage the exposure system. Exemplary photolysis is shown below.

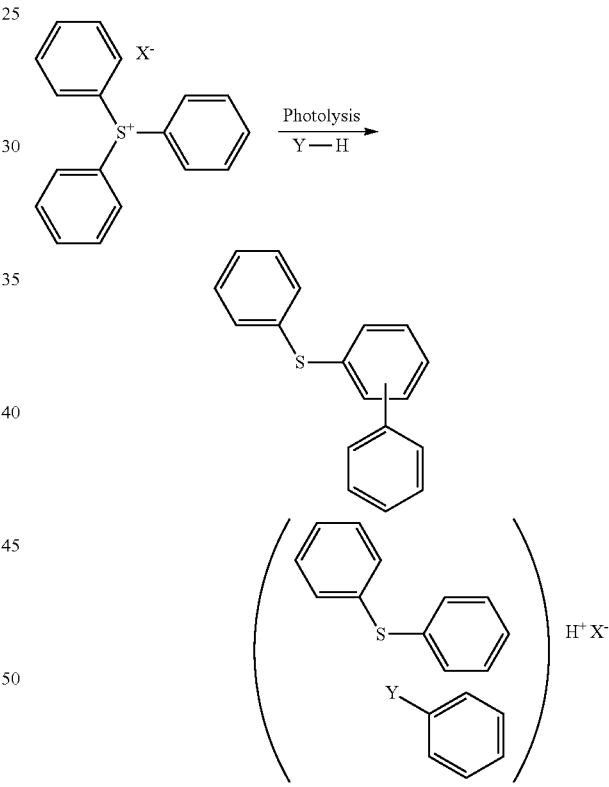

Herein Y—H designates a proton donor such as a polymer matrix. This photolysis product is exemplary while more complex photolysis products can be formed. The attempt to reduce the outgassing from acid generators is described, for example, in JP-A 2009-037057.

CITATION LIST

Patent Document 1: JP-A 2009-037057 (US 2009047598, KR 20090013727)
Non-Patent Document 1: Journal of Photopolymer Science and Technology, Vol. 17, No. 4, p 587 (2004)

SUMMARY OF INVENTION

An object of the present invention is to provide (1) a sulfonium salt, (2) a resist composition comprising the sulfonium salt, which composition exhibits a high resolution when processed by the photolithography using high-energy radiation, typically ArF excimer laser radiation or EUV radiation as the light source, and (3) a patterning process using the resist composition.

The inventors have found that a resist composition comprising a sulfonium salt having a sulfo group in the molecule, represented by the general formula (1) below, as a photoacid generator is improved in resolution and best suited for precise micropatterning.

In a first aspect, the invention provides a sulfonium salt having the general formula (1):

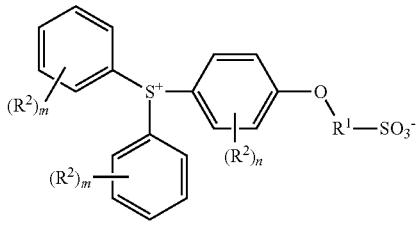

(1)

wherein $R^1$ is a $C_1$-$C_{10}$ alkylene or $C_6$-$C_{10}$ arylene group which may be substituted with fluorine or another heteroatom, $R^2$ is each independently methyl, tert-butyl, methoxy or tert-butoxy, or a linking group in the form of oxygen, methylene or sulfone or a direct bond between different benzene rings, m is an integer of 0 to 5, and n is an integer of 0 to 4.

A typical embodiment relates to a sulfonium salt having the general formula (2):

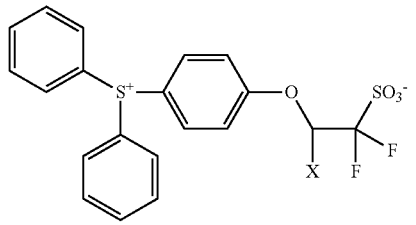

(2)

wherein X is hydrogen or trifluoromethyl.

In a second aspect, the invention provides a chemically amplified resist composition comprising the sulfonium salt defined above. Typically the resist composition comprising the sulfonium salt is positive.

In a third aspect, the invention provides a pattern forming process comprising the steps of applying the resist composition defined above onto a substrate to form a coating, heat treating the coating and exposing it to high-energy radiation through a photomask, optionally heat treating the exposed coating and developing it with a developer.

Another embodiment is a pattern forming process comprising the steps of applying the resist composition defined above onto a substrate to form a resist coating, heat treating the resist coating, applying onto the resist coating a protective film which is insoluble in water and soluble in an alkaline developer, exposing the coated substrate to high-energy radiation from a projection lens through a photomask while holding water between the substrate and the projection lens, optionally heat treating the exposed coating and developing it with a developer.

A further embodiment is a pattern forming process comprising the steps of applying the positive resist composition defined above onto a substrate to form a coating, heat treating the coating, imagewise writing with an electron beam, optionally heat treating the coating, and developing it with a developer.

A still further embodiment is a pattern forming process comprising the steps of applying the positive resist composition defined above onto a substrate to form a coating, heat treating the coating, exposing the coating to soft x-ray having a wavelength of 3 to 15 nm, optionally heat treating the coating, and developing it with a developer.

It is noted that the resist composition of the invention can be applied to the immersion lithography. The immersion lithography involves prebaking a resist film and exposing the resist film to light through a projection lens with a liquid medium interposed between the resist film and the projection lens. The ArF immersion lithography generally uses pure water as the immersion medium. This technology, combined with a projection lens having a NA of at least 1.0, is important for the ArF lithography to survive to the 65-nm node and forth, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when a polymer blend containing a hydrogenated cycloolefin ROMP polymer having a low Tg is used.

ADVANTAGEOUS EFFECTS OF INVENTION

Unlike conventional sulfonium salts, the sulfonium salt of the invention has a triphenylsulfonium cation (or photoacid generation moiety) and an anion within the molecule. It is little leached out in water when the immersion lithography is applied. While it generates a sulfonic acid upon exposure to high-energy radiation, the sulfonic acid may facilitate efficient scission of acid labile groups in chemically amplified positive resist compositions or promote acid-catalyzed crosslinking reaction in the case of chemically amplified negative resist compositions. Because of the inclusion of a triphenylsulfonium cation (or photoacid generation moiety) and an anion within a common molecule, useless volatile diphenylsulfides are not produced after the acid generation. Since the diphenylsulfide moiety forms a part of the structure of generated acid, the release of volatile matter is minimized. Because of substantial non-volatility under high vacuum conditions encountered in the EB or EUV lithography, the risk of the exposure tool being contaminated is minimized. Therefore, the sulfonium salt is best suited as a photoacid generator in chemically amplified resist compositions.

DESCRIPTION OF EMBODIMENTS

Figure 1:
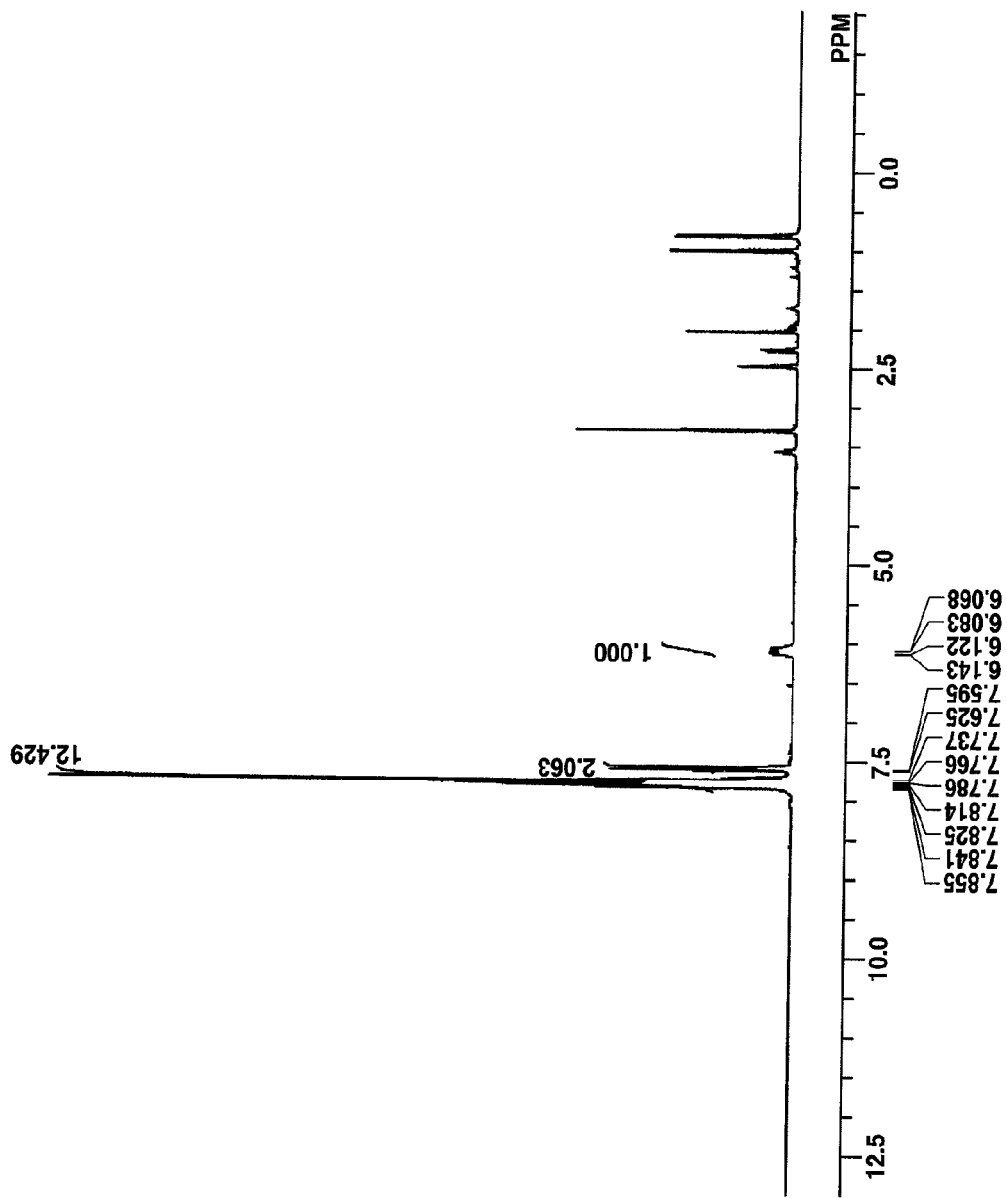
FIG. 1 is a diagram showing the $^1$H-NMR/DMSO-$d_6$ spectrum of PAG-1 in Synthesis Example 4.

As used herein, the singular forms "a," "an" and "the" include plural referents unless the context clearly dictates otherwise. The notation (Cn—Cm) means a group containing from n to m carbon atoms per group. The term "coating" is used interchangeably with "film" or "layer." The term "high-energy radiation" is intended to encompass UV, deep UV, EUV, electron beam, x-ray, excimer laser, γ-ray and synchrotron radiation.

Sulfonium Salt

In the first aspect, the invention provides a sulfonium salt having the following general formula (1).

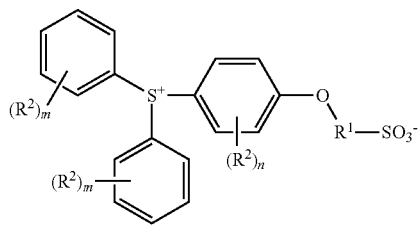

(1)

Herein $R^1$ is a $C_1$-$C_{10}$ alkylene or $C_6$-$C_{10}$ arylene group which may be substituted with fluorine or another heteroatom, $R^2$ is independently in each occurrence methyl, tert-butyl, methoxy or tert-butoxy, or a linking group in the form of oxygen, methylene or sulfone or a direct bond between different benzene rings, m is an integer of 0 to 5, and n is an integer of 0 to 4.

In formula (1), $R^1$ is a $C_1$-$C_{10}$ alkylene or $C_6$-$C_{10}$ arylene group which may be substituted with fluorine or another heteroatom. In the case of substitution with the other heteroatom, suitable substituent groups include alkoxy groups of 1 to 3 carbon atoms. As used herein, the term "heteroatom" refers to atoms other than carbon and hydrogen. The preferred heteroatoms include oxygen, nitrogen and sulfur atoms. Oxygen substitution may take the form of ether linkages such as alkoxy and aryloxy groups, or carbon-oxygen double bonds such as carbonyl groups and ester bonds. The alkylene group may be straight, branched or cyclic. Examples of the alkylene and arylene groups are shown below. In order to avoid the linkage of the group between the oxygen atom and the sulfo group from becoming vague, exemplary groups are depicted together with the oxygen atom and sulfo group.

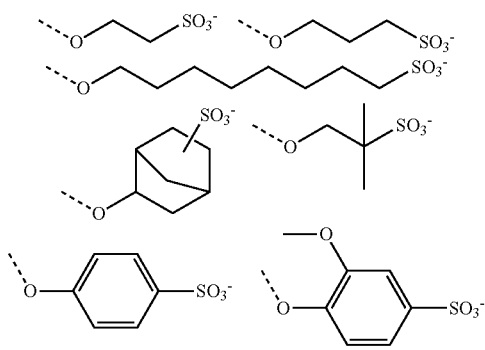

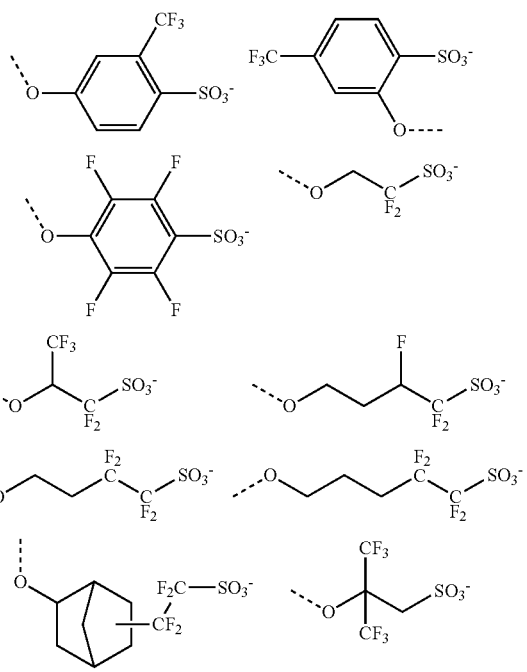

Herein the broken line designates a valence bond to the diarylsulfoniophenyl group.

Preferably $R^1$ is an alkylene group as illustrated above, with the following groups being more preferred.

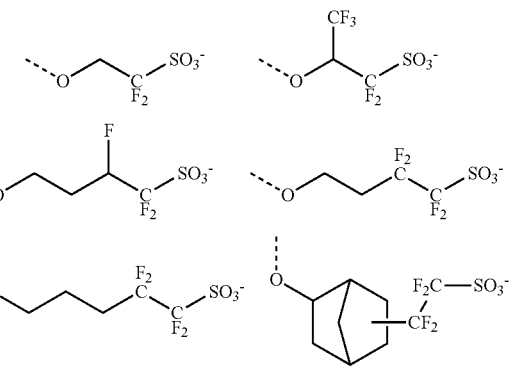

Herein the broken line designates a valence bond to the diarylsulfoniophenyl group.

$R^2$ is independently in each occurrence a methyl, tert-butyl, methoxy or tert-butoxy group. Alternatively, $R^2$ is a linking group in the form of oxygen, methylene or sulfone or a direct bond between different benzene rings, wherein $(R^2)_m$ on one benzene ring to be linked is —O—, —$CH_2$—, —$SO_2$— or a single bond whereas m=0 applies to $(R^2)_m$ on the other benzene ring. The subscript m is an integer of 0 to 5, and n is an integer of 0 to 4.

Preferably, $R^2$ is methyl or tert-butyl, m is 0 or 1, and n is 0 or 1.

As illustrative examples of the cation, exemplary sulfonium cations are depicted below as being detached from the sulfoalkyloxy or sulfoaryloxy group.

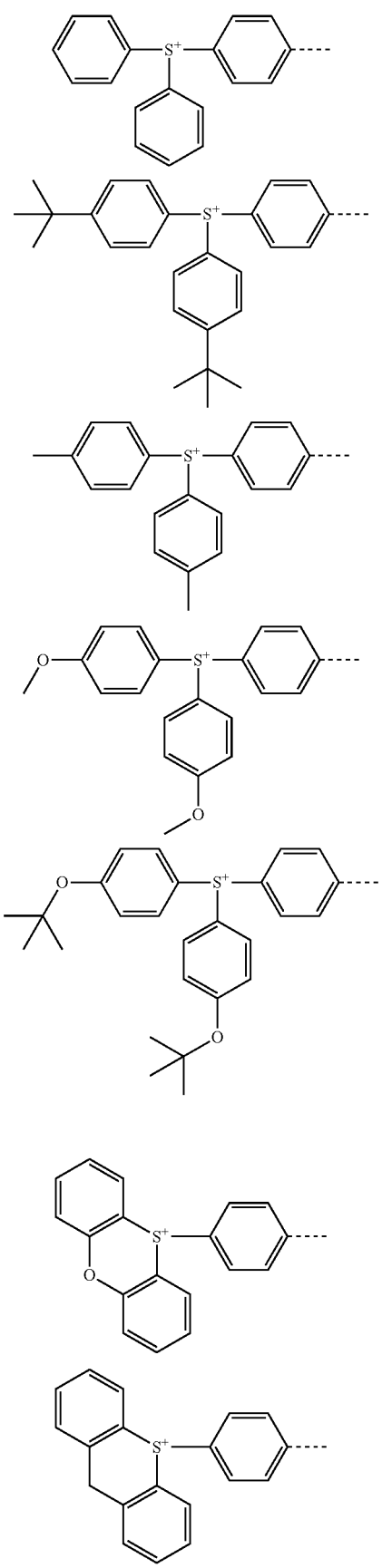

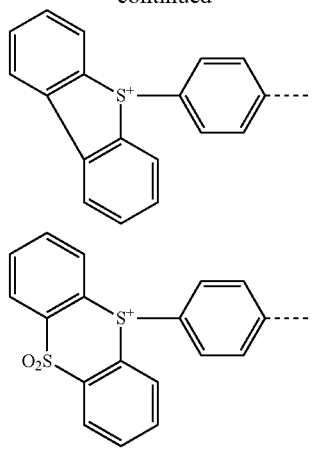

Herein the broken line designates a valence bond to the sulfoalkyloxy or sulfoaryloxy group.

Also provided herein is a sulfonium salt having the general formula (2).

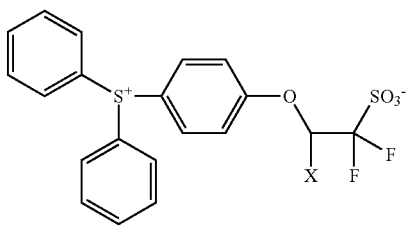
(2)

Herein X is hydrogen or trifluoromethyl.

The method for synthesizing the sulfonium salt of formula (1) or (2) is generally divided into two modes. One mode is reaction of a sulfoalkyloxybenzene or sulfoaryloxybenzene with a diarylsulfoxide in the presence of an acid catalyst. The outline of the reaction scheme is shown below.

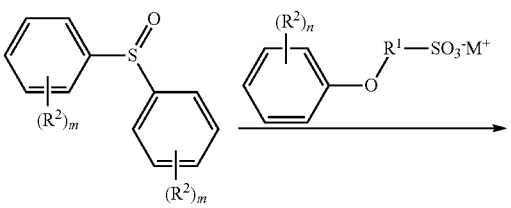

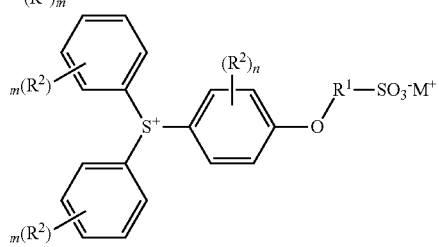

Herein $R^1$, $R^2$, m and n are as defined above, and $M^+$ is a sodium, potassium or hydrogen ion. In this mode, an acid catalyst such as methanesulfonic acid-diphosphorus pentoxide is used.

The other mode is nucleophilic displacement reaction of a 4-fluorophenyldiphenylsulfonium with a sulfoalcohol. The reaction scheme is outlined below.

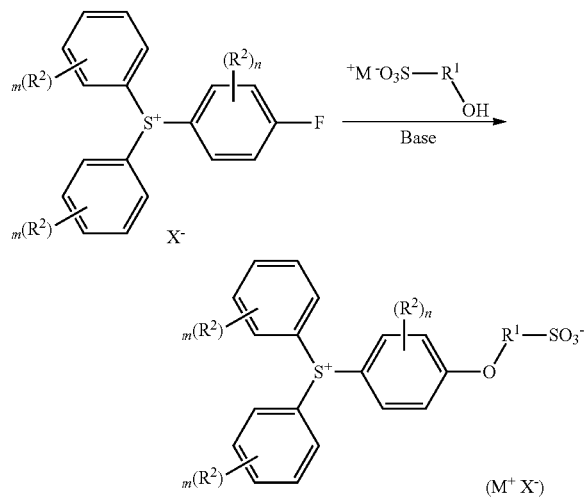

Herein $R^1$, $R^2$, m and n are as defined above, $M^+$ is a sodium, potassium or hydrogen ion, and $X^-$ is an anion such as chloride ion, bromide ion or p-toluenesulfonate. Although the 4-fluorophenyldiphenylsulfonium is illustrated herein, analogous reaction is possible with 4-halophenyldiphenylsulfoniums.

Other possible reaction modes include addition reaction of a hydrogensulfite ion to an olefin-terminated sulfonium salt and reaction of a corresponding halide with a sulfur compound. These reaction schemes are outlined below.

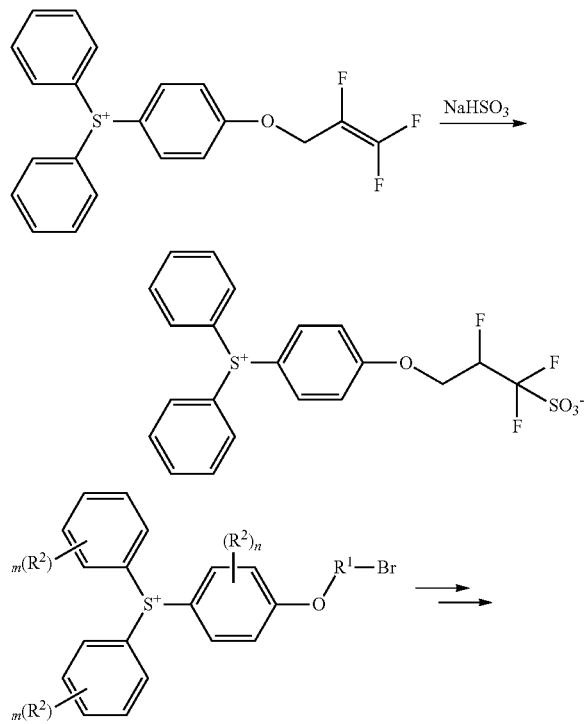

Herein $R^1$, $R^2$, m and n are as defined above.

Resist Composition

In the second aspect, the invention provides a chemically amplified resist composition comprising the sulfonium salt of formula (1) and/or (2). The resist composition may be of either positive or negative type.

One embodiment is a chemically amplified positive resist composition comprising
(A) a photoacid generator that is the sulfonium salt of formula (1) and specifically formula (2),
(B) an organic solvent,
(C) a base resin having a solubility in alkaline developer which changes under the action of acid, and optionally one or more of the following components: (D) a quencher, (S) a surfactant which is insoluble or substantially insoluble in water and soluble in alkaline developer, and/or a surfactant which is insoluble or substantially insoluble in water and alkaline developer, (E) a photoacid generator other than the inventive photoacid generator, (F) an organic acid derivative and/or fluorinated alcohol, and (G) a dissolution inhibitor having a weight average molecular weight of up to 3,000.

Another embodiment is a chemically amplified negative resist composition comprising
(A) a photoacid generator that is the sulfonium salt of formula (1) and specifically formula (2),
(B) an organic solvent,
(C') a base resin which is normally alkali soluble, but becomes substantially alkali insoluble under the action of a crosslinker,
(H) a crosslinker for inducing crosslinkage under the action of an acid, and optionally
one or more of the following components: (D) a quencher, (S) a surfactant which is insoluble or substantially insoluble in water and soluble in alkaline developer, and/or a surfactant which is insoluble or substantially insoluble in water and alkaline developer, and (E) a photoacid generator other than the inventive photoacid generator.

Now these components are described in detail.

The photoacid generator (A) is specifically the sulfonium salt of formula (1), more specifically the sulfonium salt of formula (2). In the resist composition, the photoacid generator (A) is preferably used in an amount of 0.1 to 40 parts, and more preferably 1 to 20 parts by weight per 100 parts by weight of the base resin.

Organic Solvent

The organic solvent (B) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, propylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use 1-ethoxy-2-propanol, PGMEA, cyclohexanone, ethyl lactate, and mixtures thereof because the acid generator is most soluble therein.

An appropriate amount of the organic solvent used is 200 to 5,000 parts, especially 400 to 3,000 parts by weight per 100 parts by weight of the base resin.

Base Resin

The polymers used as the base resin (C) or (C') include polyhydroxystyrene (PHS), and copolymers of hydroxystyrene with styrene, (meth)acrylic acid esters or other polymerizable olefinic compounds, for KrF excimer laser resist use; (meth)acrylic acid ester polymers, alternating copolymers of cycloolefin with maleic anhydride, copolymers further containing vinyl ethers or (meth)acrylic acid esters, polynorbornene, cycloolefin ring-opening metathesis polymerization (ROMP) polymers and hydrogenated products thereof, for ArF excimer laser resist use; and fluorinated forms of the foregoing polymers (for both KrF and ArF laser uses) for $F_2$ excimer laser resist use. The base resin is not limited to the polymers of these systems. For EB, x-ray and EUV lithography resist materials, the polyhydroxystyrene and copolymers thereof are useful.

As the base resin, the polymers may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The base resin (C) may also be selected from polymers comprising recurring units having an acid labile group of the following general formula (3) and recurring units of one or more types selected from the following general formulae (4) to (6).

(3)

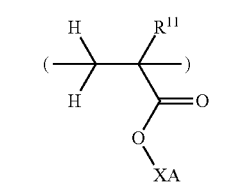

(4)

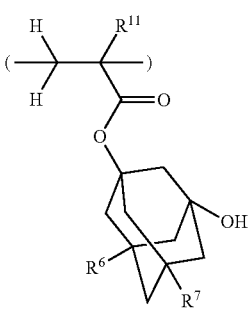

(5)

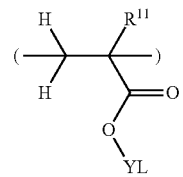

(6)

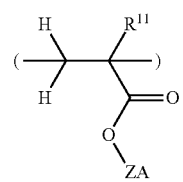

Herein $R^{11}$ is hydrogen, fluorine, methyl or trifluoromethyl. $R^6$ and $R^7$ are each independently hydrogen or hydroxyl. XA is an acid labile group. YL is a lactone structure-containing substituent group. ZA is hydrogen, $C_1$-$C_{15}$ fluoroalkyl, or $C_1$-$C_{15}$ fluoroalcohol-containing substituent group.

Under the action of an acid, a polymer comprising recurring units of formula (3) is decomposed to generate a carboxylic acid and turns into an alkali-soluble polymer.

The acid labile groups represented by XA may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

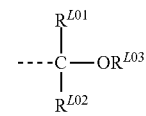

(L2)

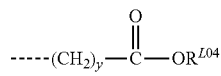

(L3)

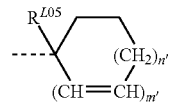

(L4)

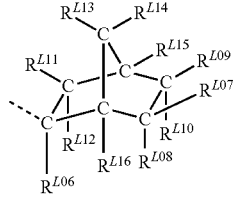

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Suitable straight, branched or cyclic alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. Examples of the substituted alkyl groups are shown below.

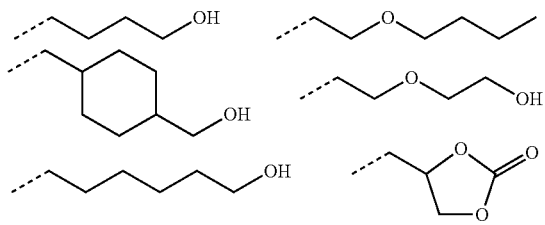

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m' is 0 or 1, n' is 0, 1, 2 or 3, and 2 m'+n' is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

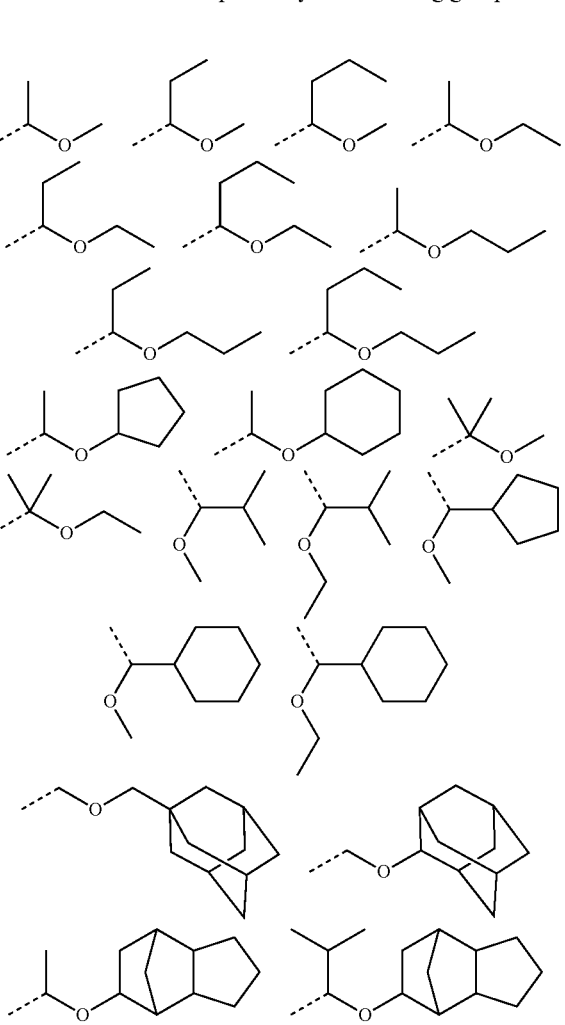

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

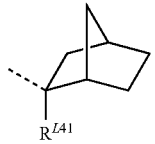
(L4-1)

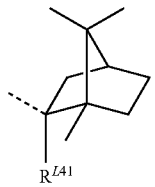
(L4-2)

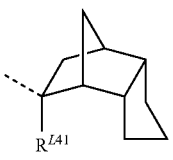
(L4-3)

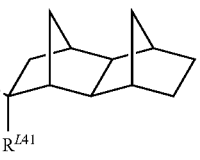
(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

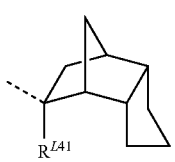
(L4-3-1)

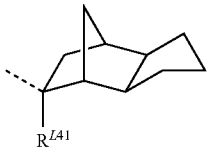
(L4-3-2)

Similarly, the general formula (L4-4) represents one or a mixture of two or more selected from groups having the following general formulas (L4-4-1) to (L4-4-4).

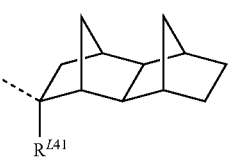
(L4-4-1)

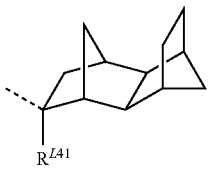
(L4-4-2)

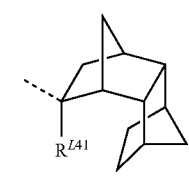
(L4-4-3)

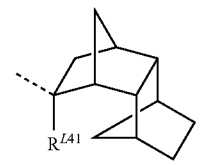
(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

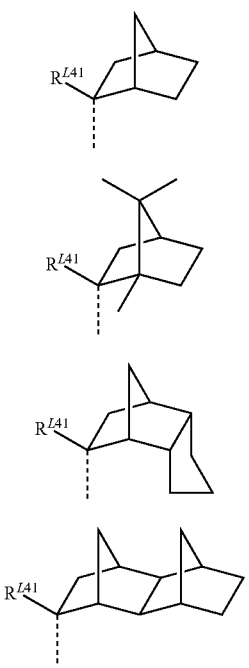
Illustrative examples of the acid labile group of formula (L4) are given below, but not limited thereto.
Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.
Illustrative, non-limiting examples of the recurring units of formula (3) are given below.
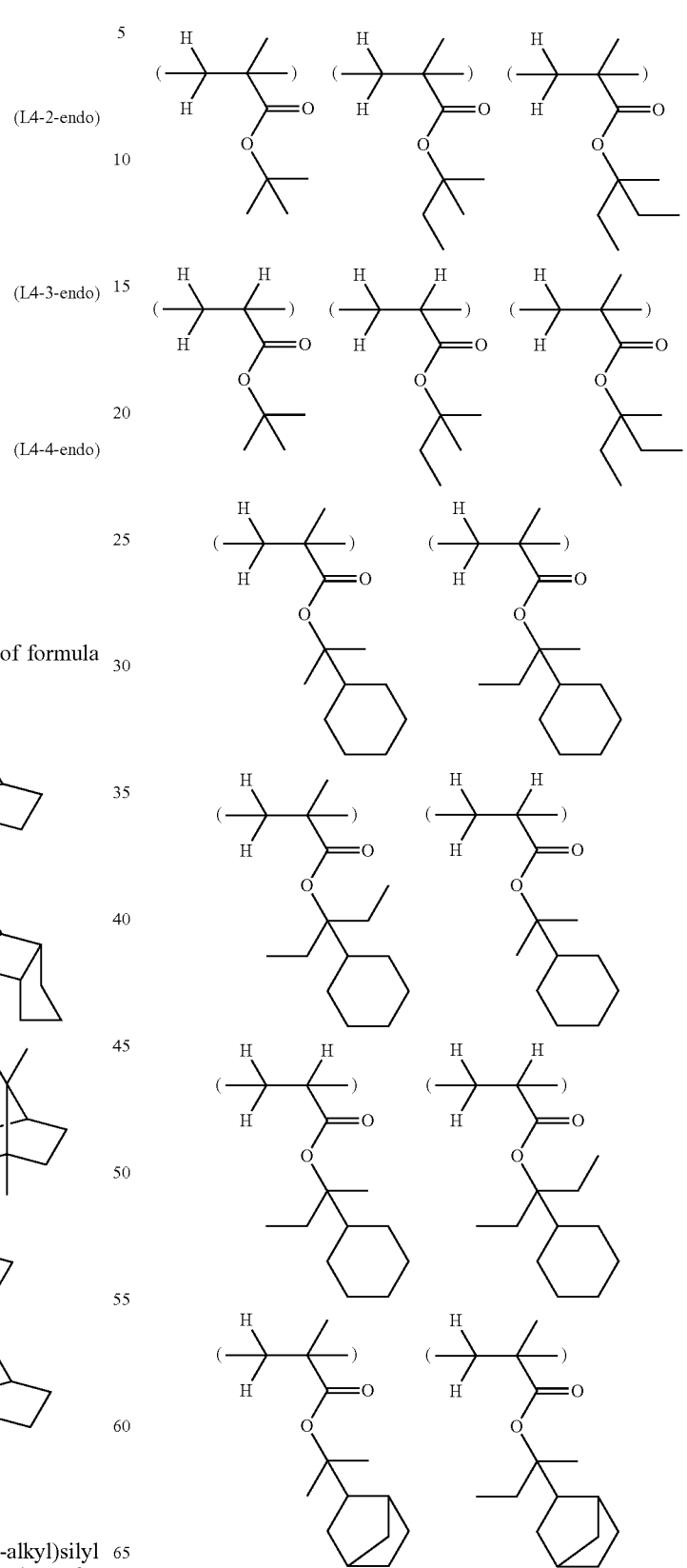

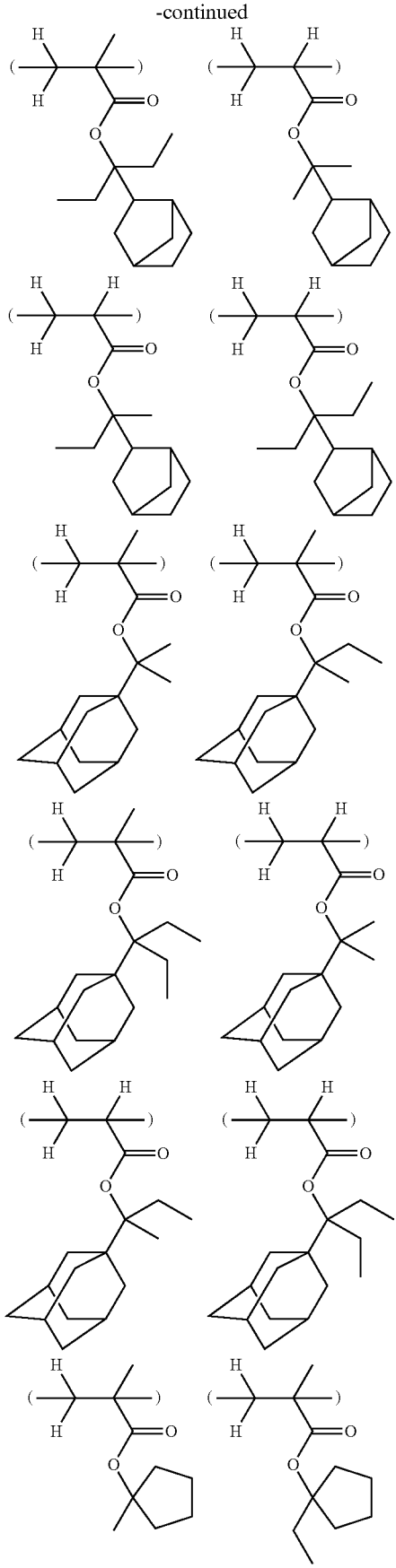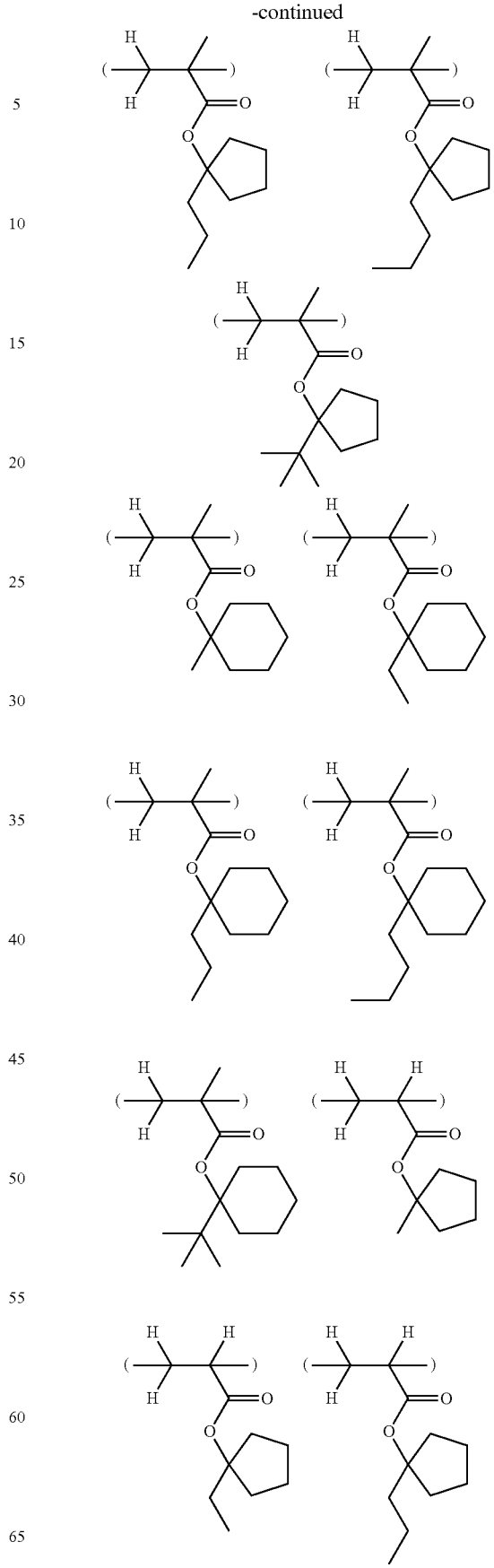

-continued
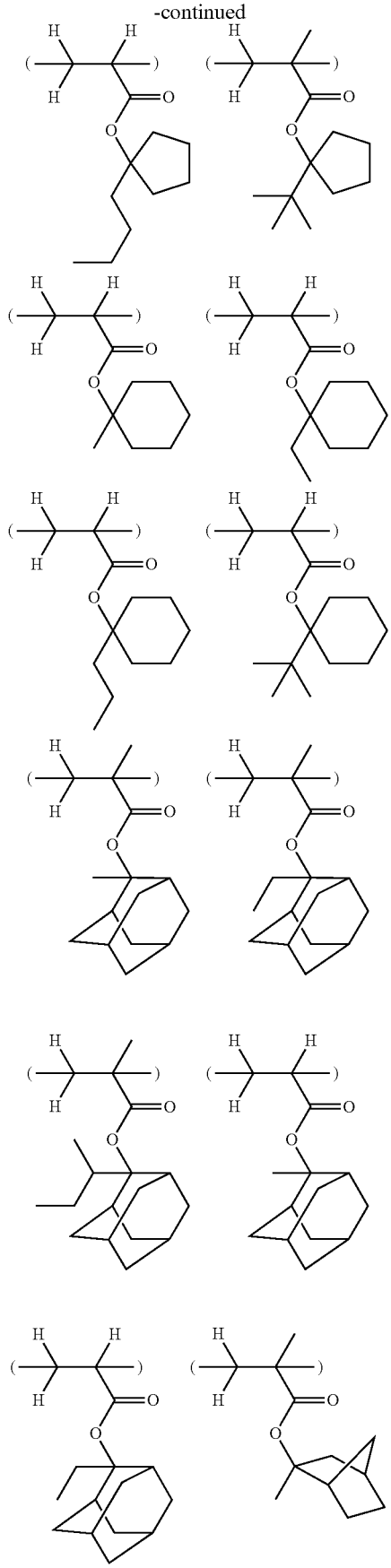
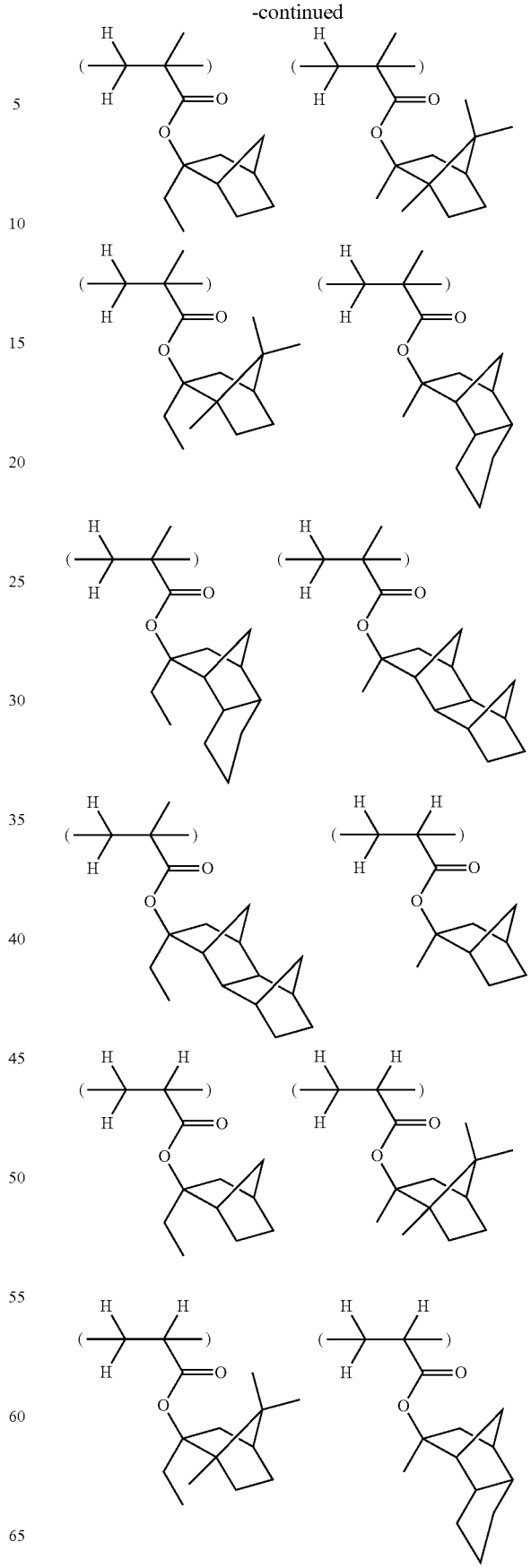

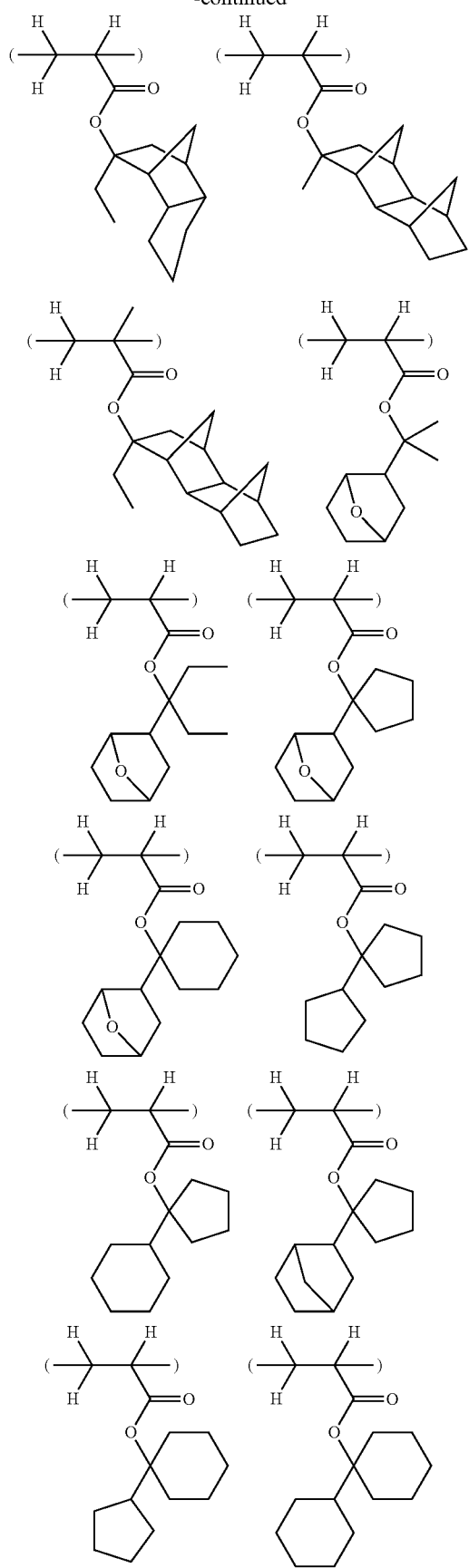
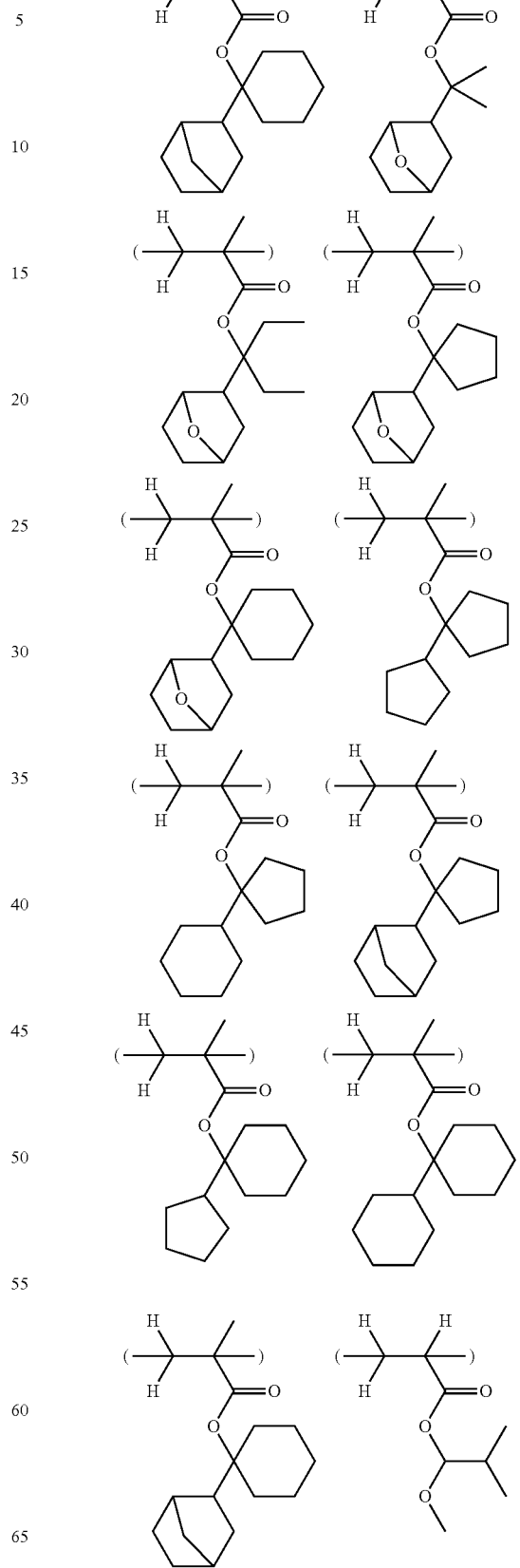

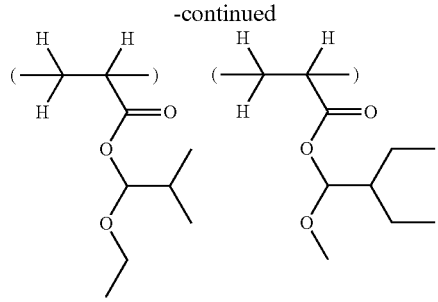
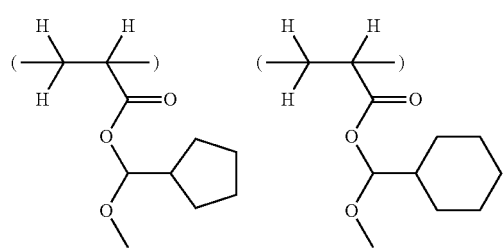
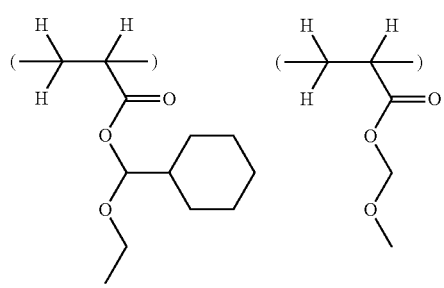
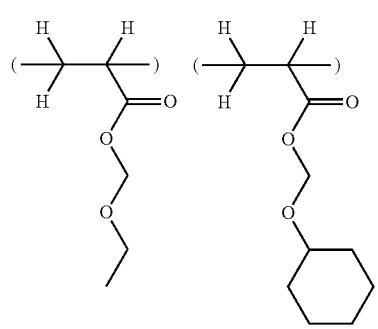
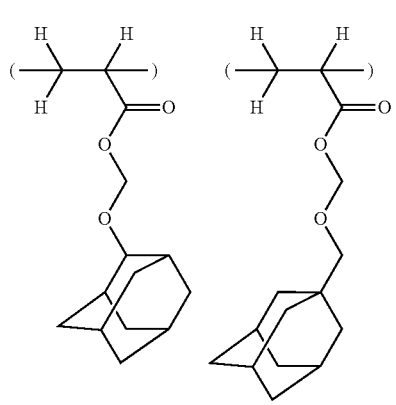
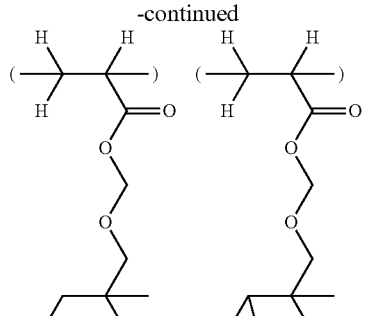
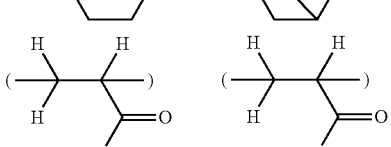
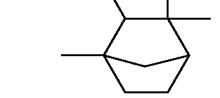
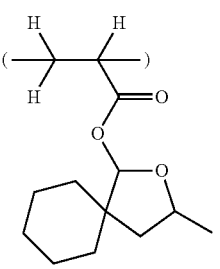
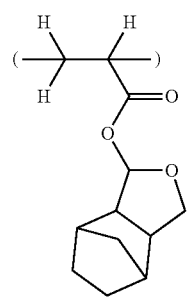
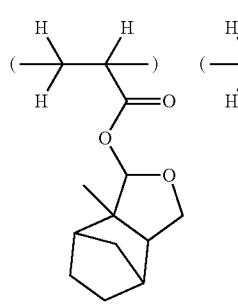

-continued
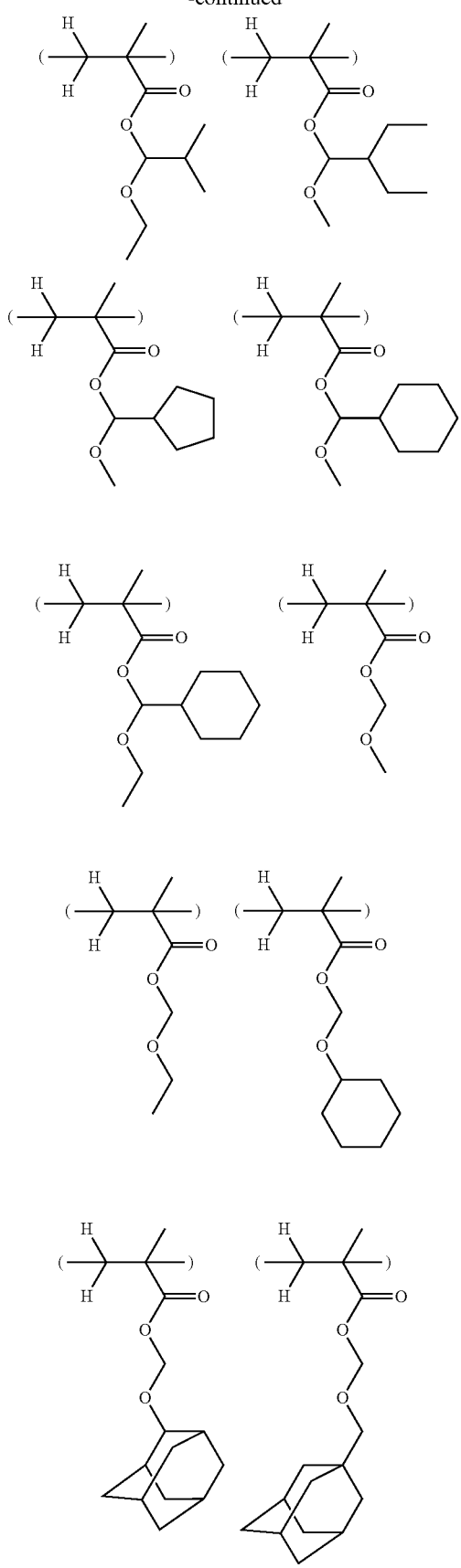
-continued
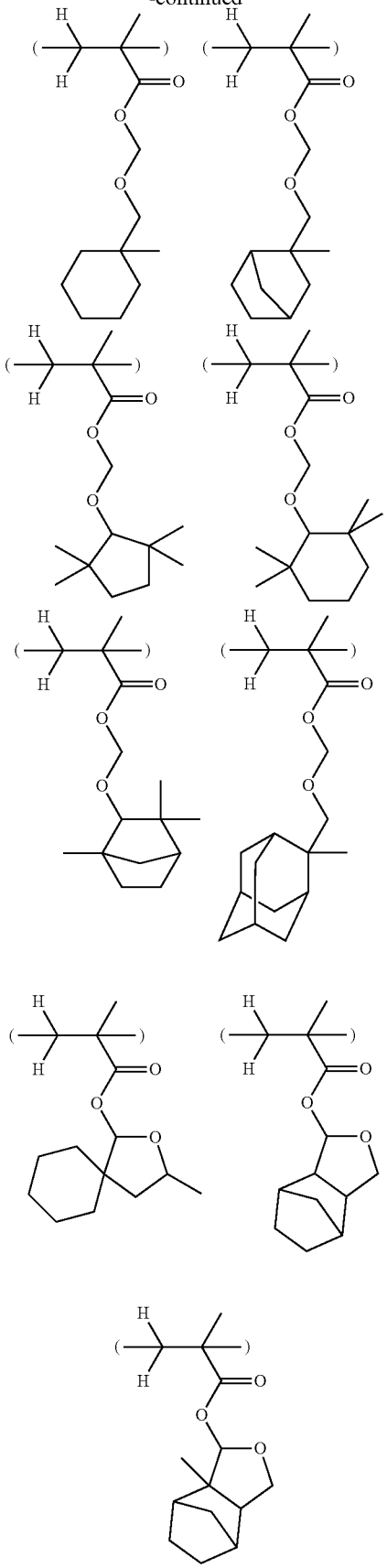

Illustrative, non-limiting examples of the recurring units of formula (4) are given below.
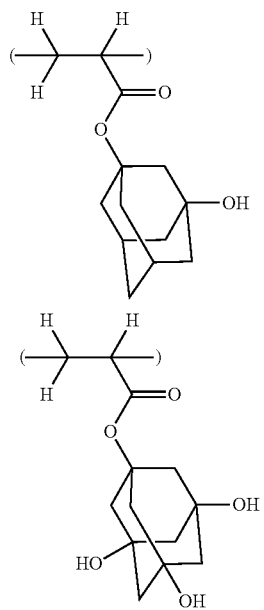 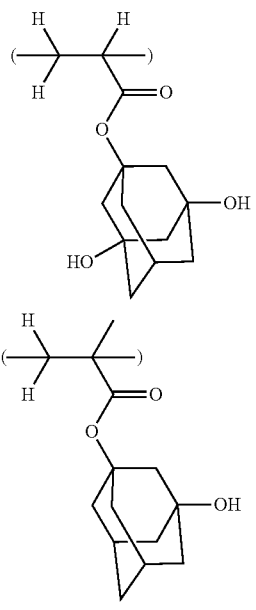
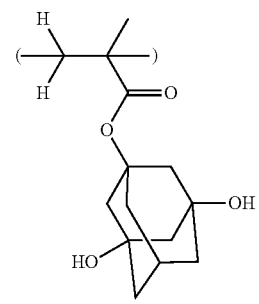 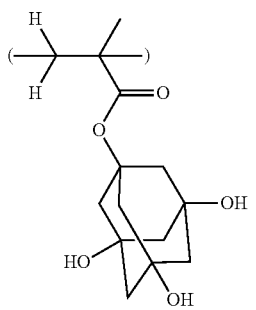
Illustrative examples of the recurring units of formula (5) are given below.
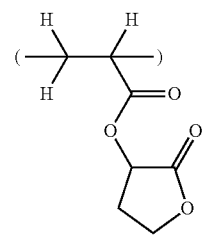 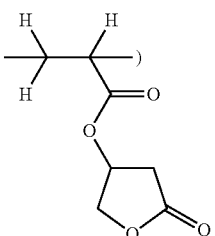
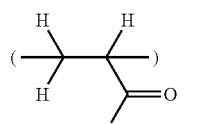 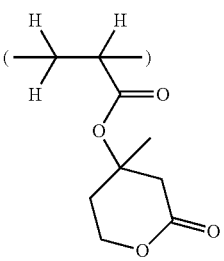
-continued
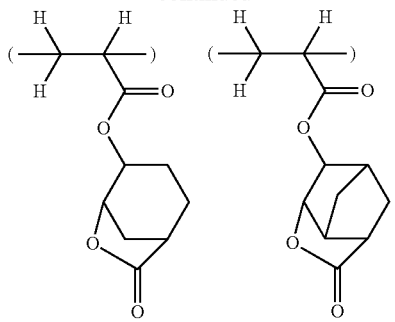 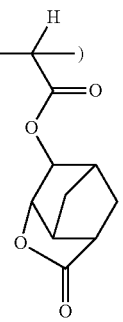
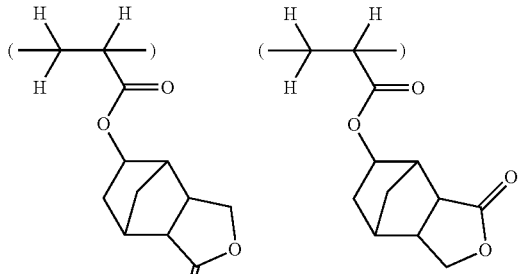 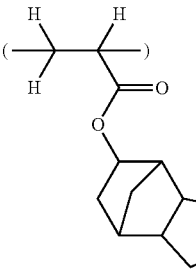
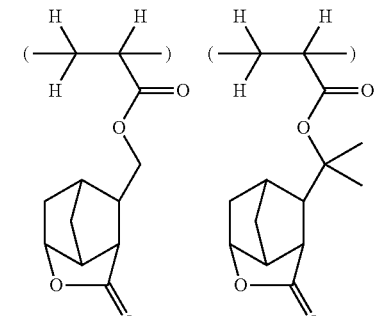 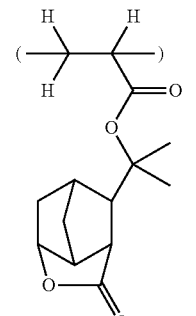
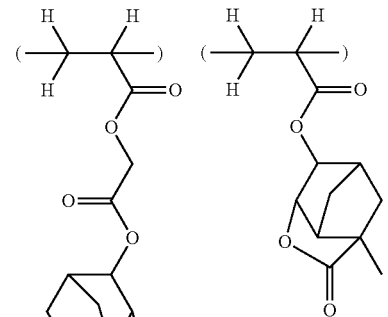 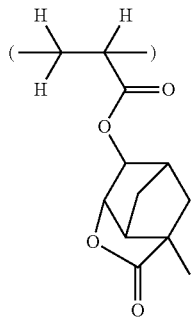

-continued
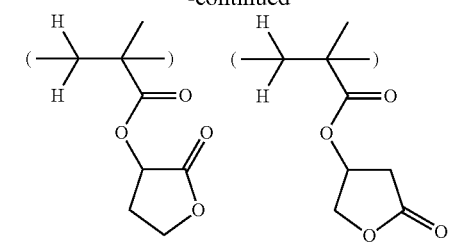
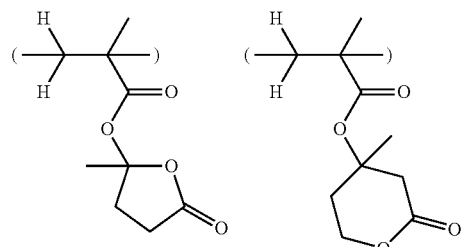
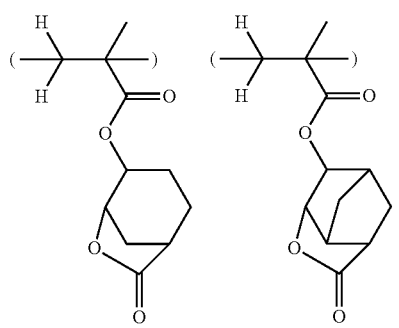
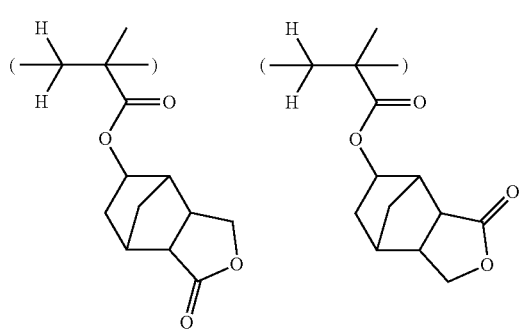
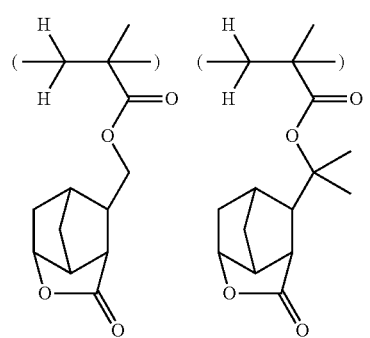
-continued
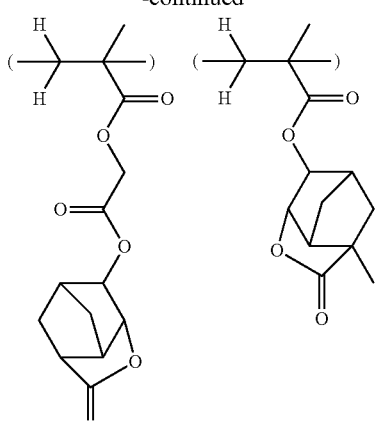
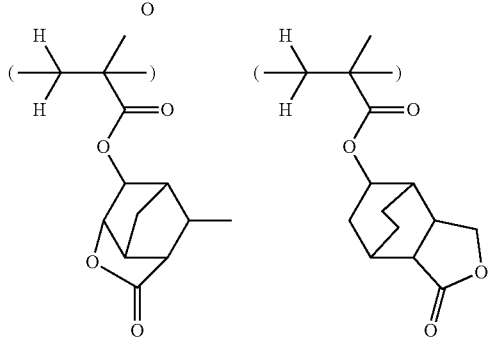
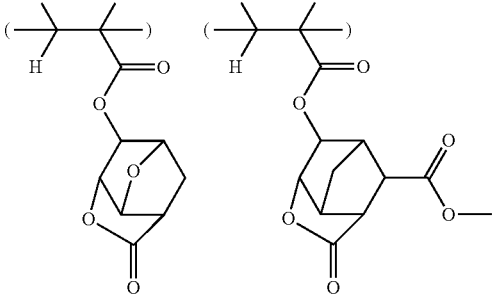
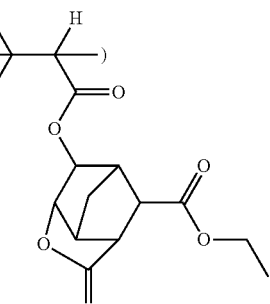
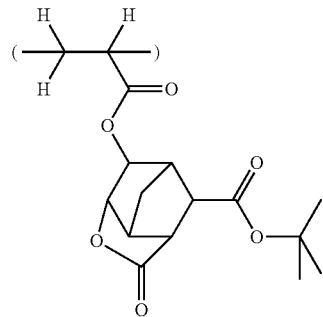

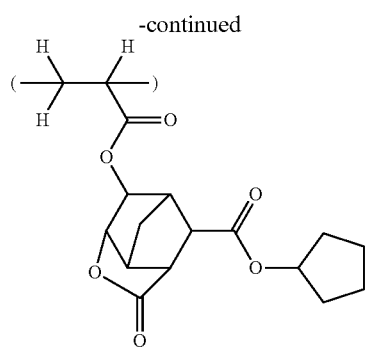
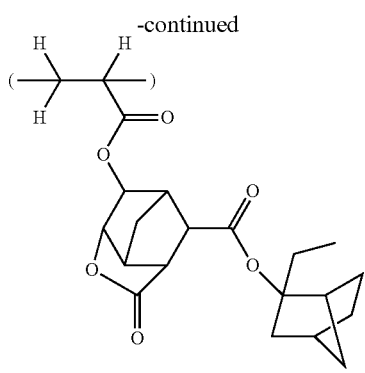
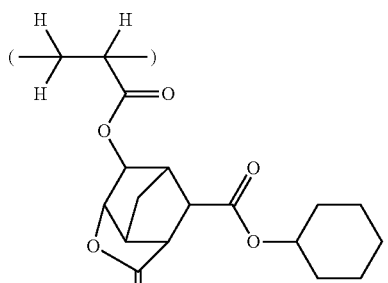
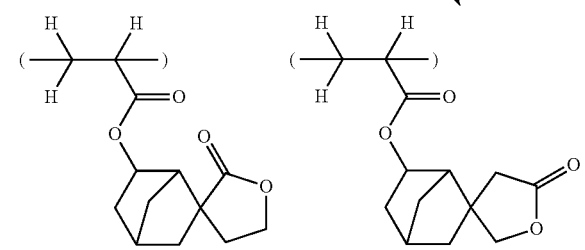
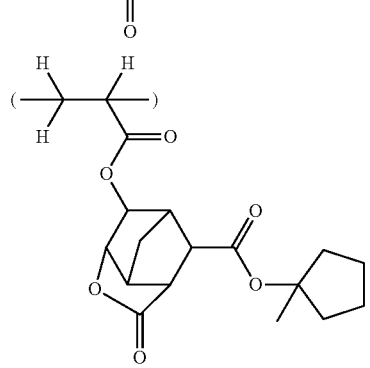
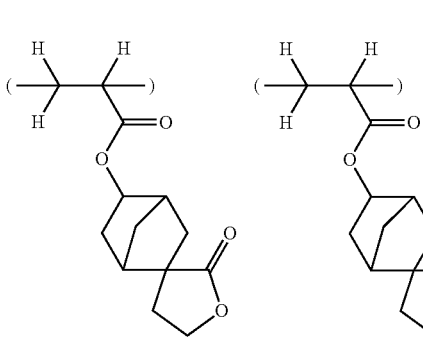
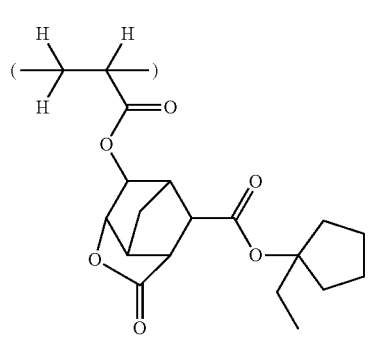
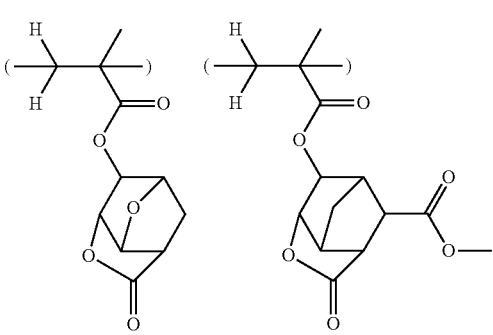
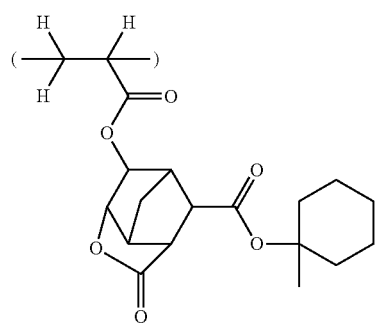
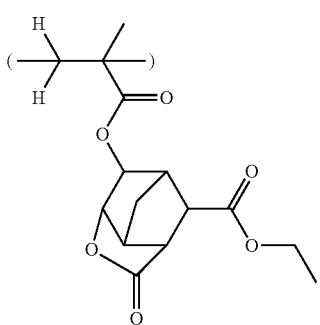

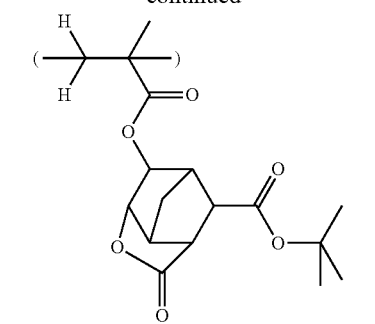
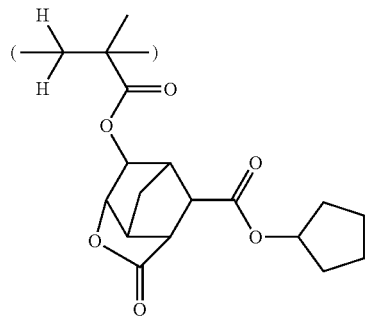
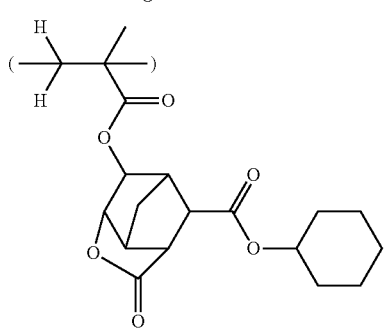
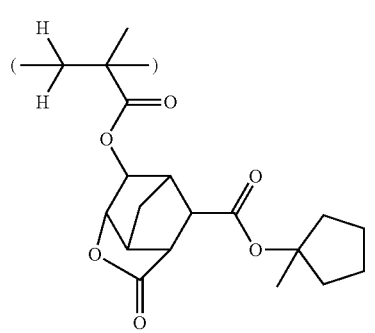
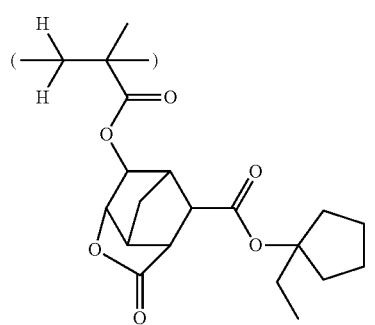
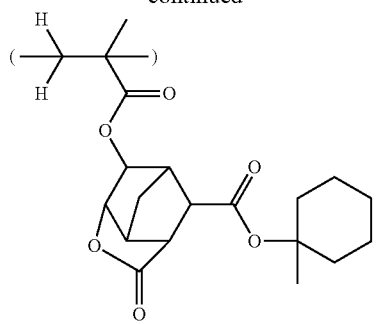
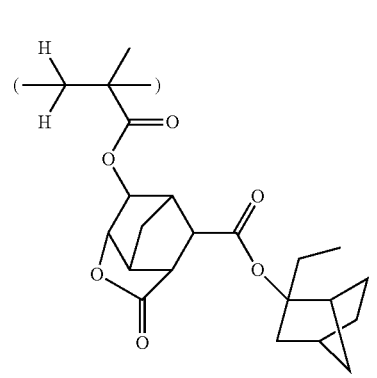
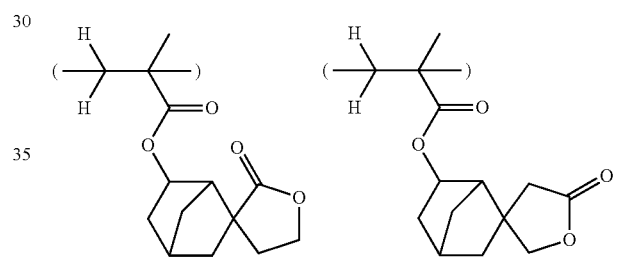
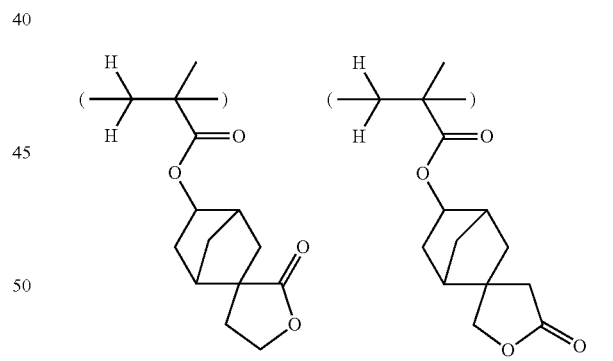
Illustrative examples of the recurring units of formula (6) are given below.
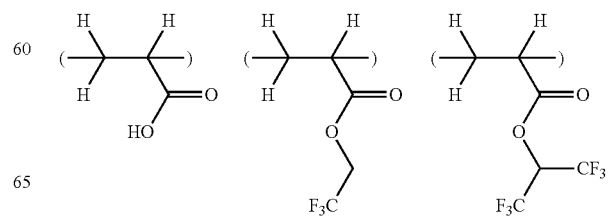

-continued
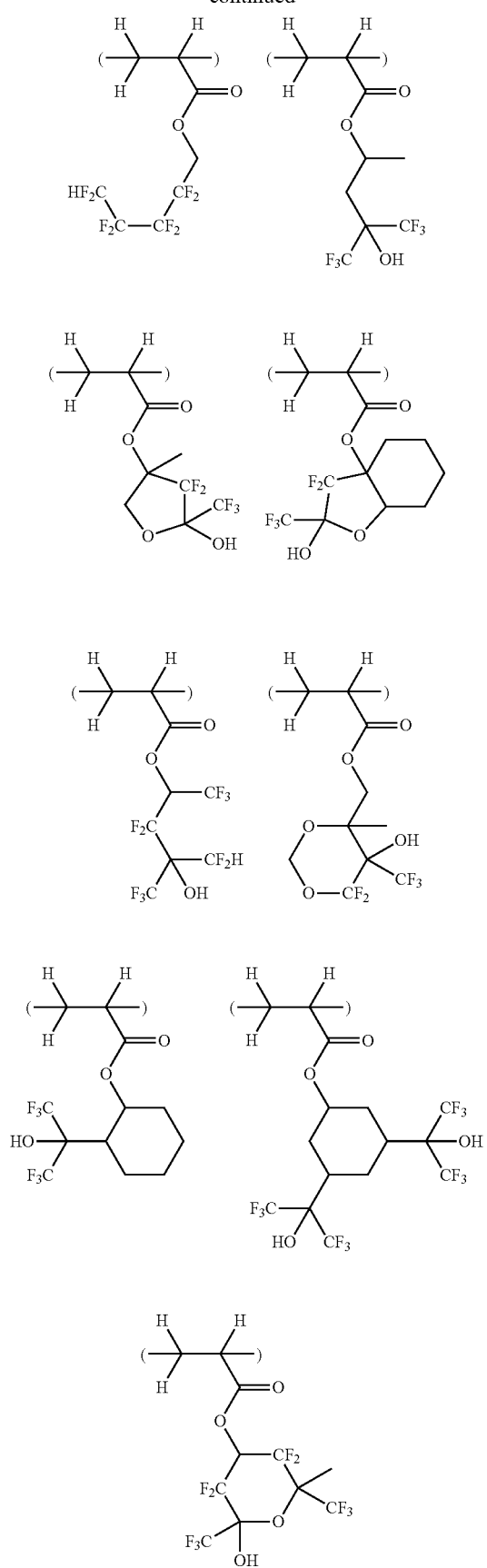
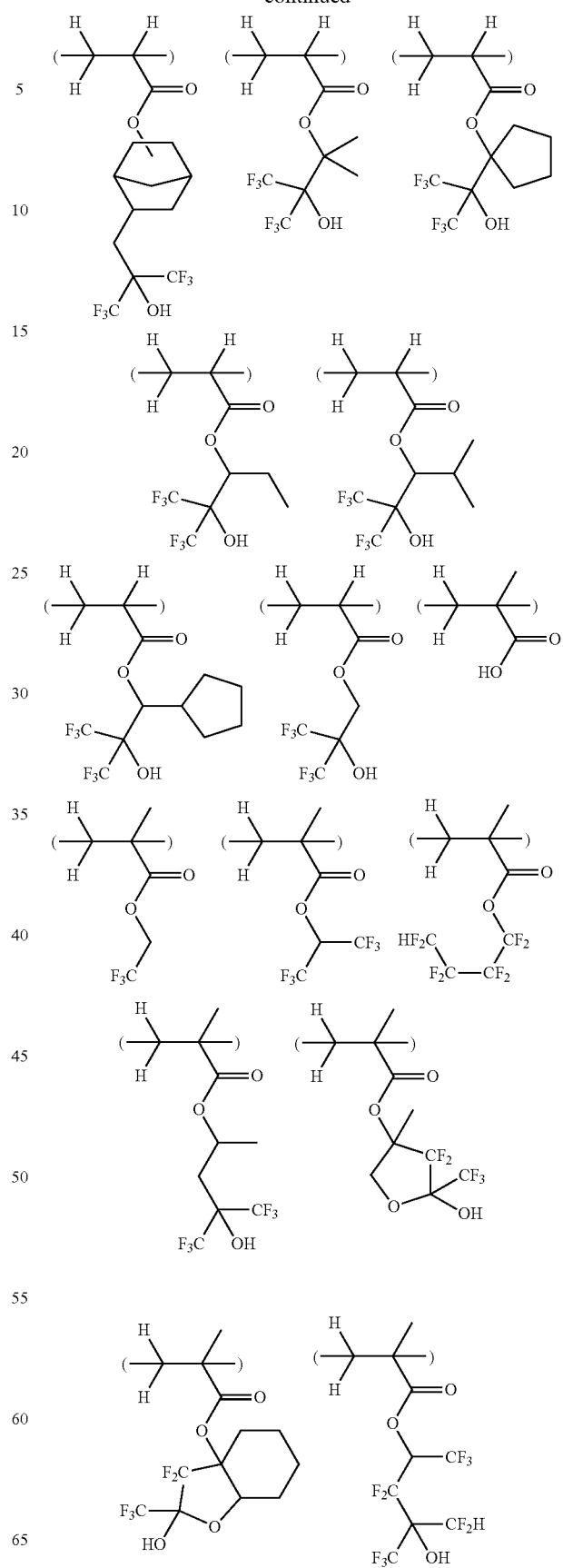

-continued

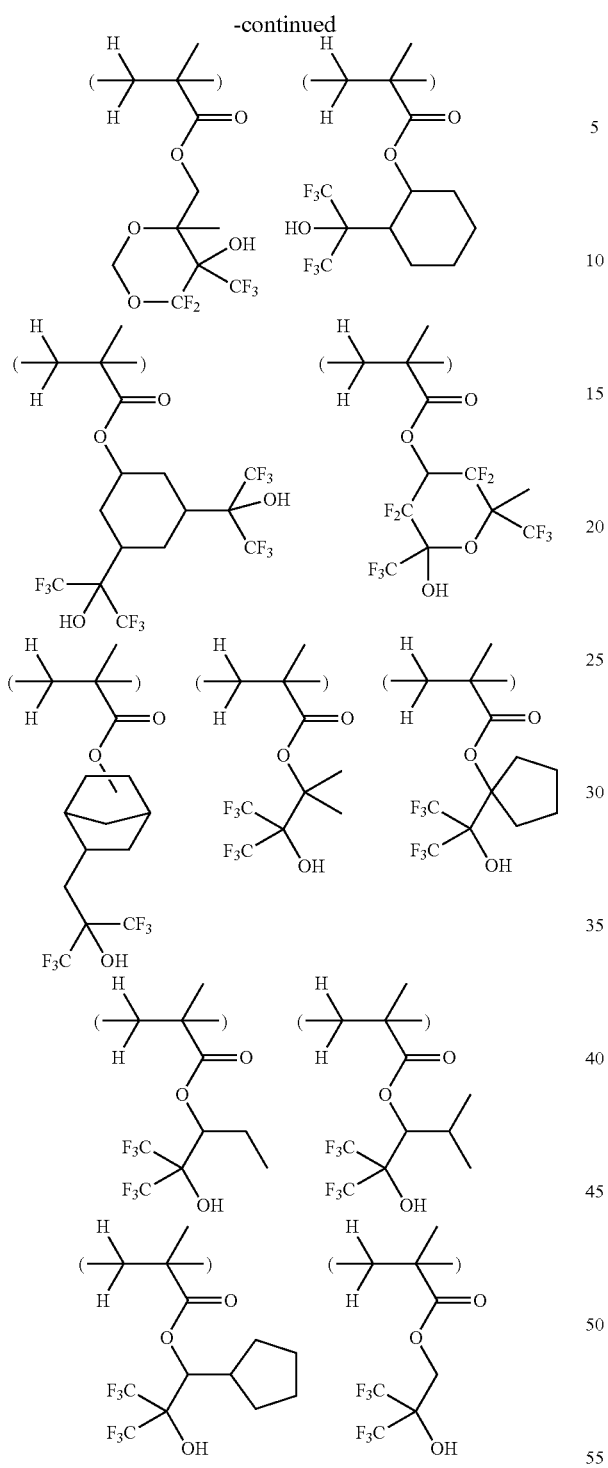

The polymer used herein may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo [6.2.1.1$^{3,6}$.0$^{2,7}$]dodecene derivatives, unsaturated acid anhydrides such as itaconic anhydride, and other monomers. Useful examples of the hydrogenated ROMP polymers are described in JP-A 2003-066612.

Although the polymers described above are preferably applied to the ArF photolithography, they may also be applied to other lithography such as KrF, EUV and EB lithography.

In an embodiment wherein the resist composition is applied to the KrF, EUV and EB lithography, the polymer as the base resin may desirably comprise recurring units of at least one type selected from the general formulae (7) to (9) and optionally, recurring units of at least one type selected from the general formulae (3) to (6).

Herein R$^{11}$ and XA are as defined above, and G is an oxygen atom or carbonyloxy group (—C(=O)O—).

Under the action of an acid, a polymer comprising recurring units of formula (7) is decomposed to generate a phenolic hydroxyl group and/or carboxylic acid whereby it becomes alkali soluble. The acid labile group XA may be selected from a variety of such groups, for example, groups of formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (7) are given below.
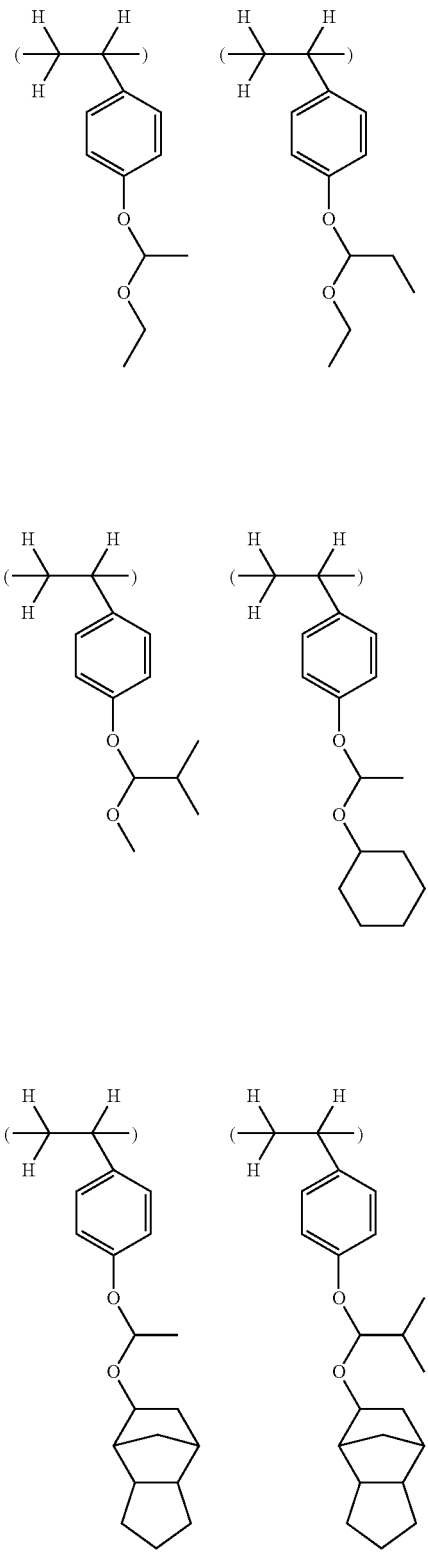
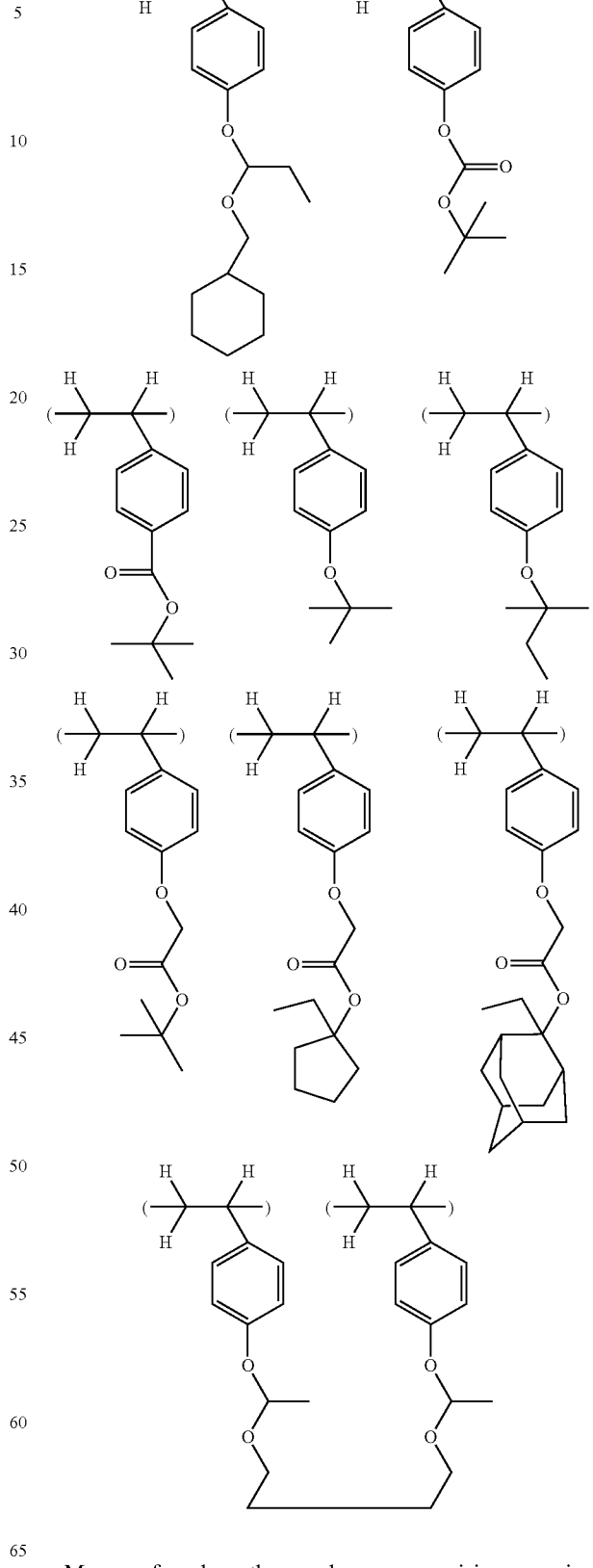
More preferred are those polymers comprising recurring units of any one type selected from formulae (7) to (9) and recurring units of any one type selected from formulae (3) to (6), especially recurring units of formula (3).

The polymer comprising recurring units of any one or more type selected from formulae (7) to (9) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$]dodecene derivatives, and norbornadiens, unsaturated acid anhydrides such as itaconic anhydride, styrene, acenaphthylene, vinylnaphthalene, and other monomers.

The polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards or the light scattering method.

In the polymer, the preferred proportion of respective recurring units derived from discrete monomers may fall, for example, in the range (mol %) shown below, but is not limited thereto. The polymer may consist essentially of (I) from more than 1 mol % to 50 mol %, preferably 5 to 40 mol %, and more preferably 10 to 30 mol % of constituent units of one or more type having formulae (3) and/or (7); (II) from 50 mol % to 99 mol %, preferably 60 to 95 mol %, and more preferably 70 to 90 mol % of constituent units of one or more type having formulae (4) to (6) and/or formulae (8) and (9); and (III) from 0 mol % to 80 mol %, preferably 0 to 70 mol %, and more preferably 0 to 50 mol % of constituent units of one or more type derived from the additional monomer(s).

The polymer may be modified by deprotecting some or all acid labile groups so that the polymer may be used in negative resist compositions as will be described later. Into the polymer in which acid labile groups have been deprotected, different acid labile groups may be introduced again. This indicates that acid labile groups different from the acid labile groups initially introduced during polymerization are introduced into the polymer.

For example, once a polymer is formed through radical polymerization of 4-ethoxyethoxystyrene with another polymerizable compound, the polymer may be tailored into a copolymer with hydroxystyrene by eliminating ethoxyethoxy groups from the polymer using acetic acid, pyridinium tosylate or the like. The tailored copolymer may be used as a base resin in negative resist compositions. By further reacting hydroxystyrene units of the copolymer with di-tert-butyl dicarbonate, tert-butyl chloroacetate, vinyl ether or the like, acid labile groups different from the acid labile groups (ethoxyethoxy) initially introduced during polymerization may be introduced into the copolymer.

The polymer is not limited to one type and a mixture of two or more polymers may be added. The use of plural polymers allows for easy adjustment of resist properties.

Quencher

A quencher (D) may be optionally used in the resist composition. The term "quencher" as used herein refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of the quencher are described in JP-A 2008-102383 and JP-A 2009-080474. Of these, tertiary amines having a polar functional group such as ether, carbonyl, ester or alcohol, amine oxides, benzimidazoles, and anilines are preferred.

Preferred tertiary amines include 2-morpholinoethyl esters of straight, branched or cyclic $C_2$-$C_{20}$ aliphatic carboxylic acids and trialkylamines having a straight, branched or cyclic $C_2$-$C_{10}$ alkyl moiety. In these amines, some carbon-bonded hydrogen atoms may be replaced by hydroxyl groups, or these amines may have an ether or ester linkage. Examples include 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl cyclohexanecarboxylate, 2-morpholinoethyl adamantanecarboxylate, 4-[2-[(2-methoxyethoxy)methoxy]ethyl]morpholine, 4-[2-[2-(2-methoxyethoxy)ethoxy]ethyl]morpholine, 4-[2-[2-(2-butoxyethoxy)ethoxy]ethyl]morpholine, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, and tris(2-pivaloyloxyethyl)amine.

Of the amine oxides, N-oxides resulting from oxidation of the foregoing tertiary amines are preferred. Examples include tris(2-(methoxymethoxy)ethyl)amine oxide, 2,2',2''-nitrilotriethylpropionate N-oxide, and N-2-(2-methoxyethoxy)methoxyethylmorpholine N-oxide.

Preferred examples of benzimidazoles include benzimidazole, 2-phenylbenzimidazole, 1-(2-acetoxyethoxy)benzimidazole, 1-[2-(methoxymethoxy)ethyl]benzimidazole, 1-[2-(methoxymethoxy)ethyl]-2-phenylbenzimidazole, and 1-(2-(2-methoxyethoxy)ethoxy)ethyl)benzimidazole.

Preferred examples of anilines include aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine.

The quenchers may be used alone or in admixture of two or more. The quencher is preferably used in an amount of 0.001 to 8 parts, more preferably 0.01 to 4 parts by weight per 100 parts by weight of the base resin. Less than 0.001 phr of the quencher may achieve no addition effect whereas more than 8 phr may lead to too low a sensitivity.

Photoacid Generator

In combination with the inventive photoacid generator, another photoacid generator is used as component (E) if desired. The auxiliary photoacid generator used herein may be any compound capable of generating an acid upon exposure to high-energy radiation such as UV, deep UV, EUV, EB, x-ray, excimer laser, γ-ray or synchrotron radiation. Suitable photoacid generators include sulfonium salts, iodonium salts, sulfonyldiazomethane, N-sulfonyloxydicarboxylmide, O-arylsulfonyloxime, and O-alkylsulfonyloxime acid generators. The photoacid generators may be used alone or in admixture of two or more.

Exemplary photoacid generators are described in JP-A 2009-080474. Illustrative examples are shown below.

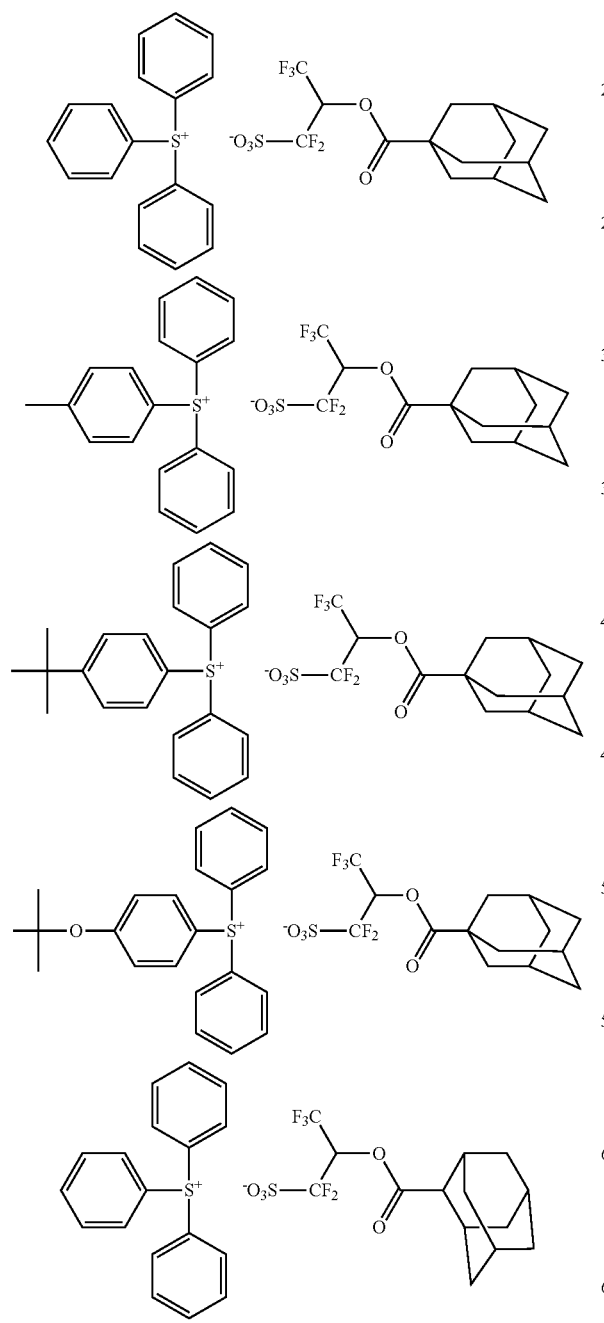

-continued

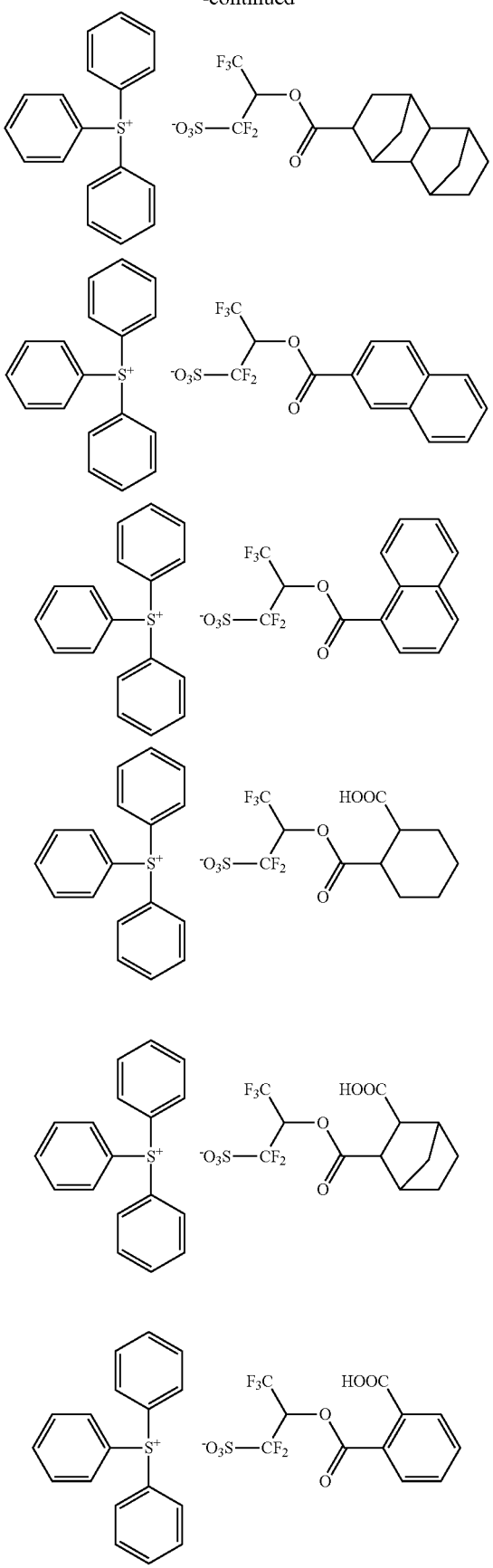

47

-continued

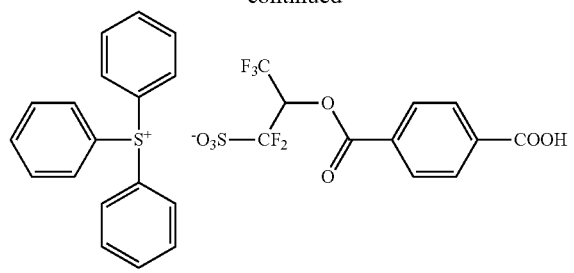

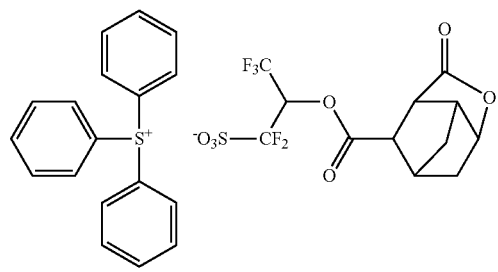

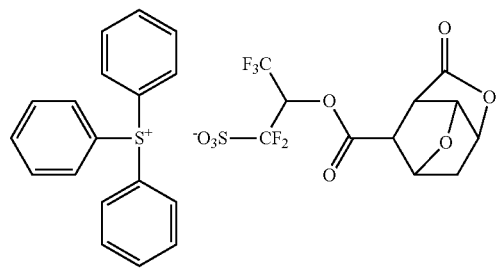

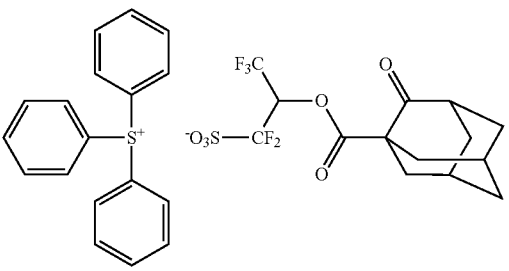

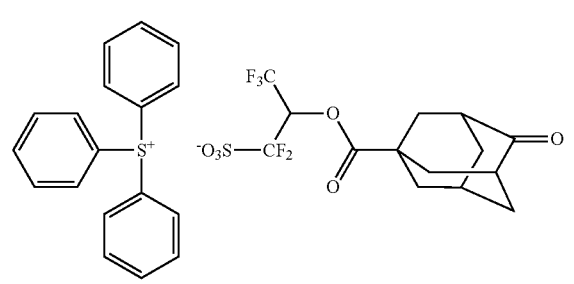

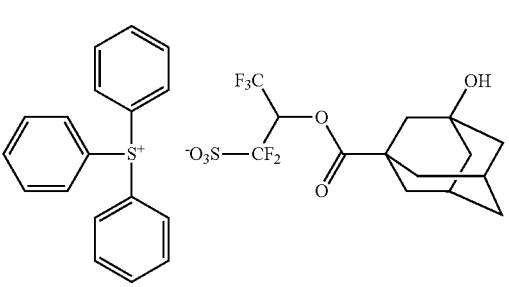

48

-continued

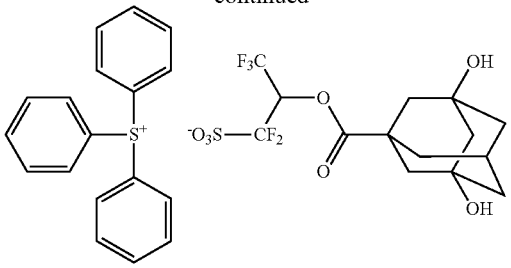

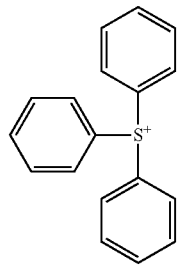

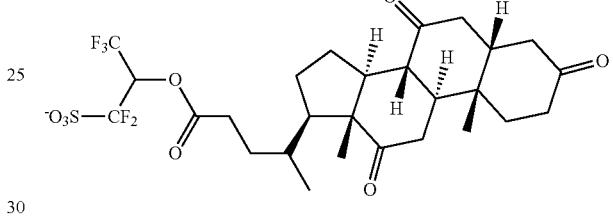

Those compounds described in JP-A 2009-007327 are also useful.

In the chemically amplified resist composition, the auxiliary photoacid generator (E) may be added in any desired amount as long as the objects of the invention are not compromised. An appropriate amount of the photoacid generator (E), when added, is 0.1 to 40 parts, and more preferably 0.1 to 20 parts by weight per 100 parts by weight of the base resin in the composition. Too high a proportion of the photoacid generator (E) may give rise to problems of degraded resolution and foreign matter upon development and resist film peeling. The photoacid generators (E) may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the resist composition, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996). Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component F

Component (F) is an organic acid derivative and/or a fluorinated alcohol. Illustrative, non-limiting, examples of the organic acid derivatives include phenol, cresol, catechol, resorcinol, pyrogallol, phloroglucin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

The fluorinated alcohol is an alcohol which is substituted with fluorine atoms except α-position. Those compounds terminated with 1,1,1,3,3,3-hexafluoro-2-propanol are desirable although the fluorinated alcohols are not limited thereto. Illustrative examples of the desirable fluorinated alcohols are described in JP-A 2009-080474.

In the chemically amplified resist composition, the organic acid derivative or fluorinated alcohol is preferably formulated in an amount of up to 5 parts, and especially up to 1 part by weight, per 100 parts by weight of the base resin. More than 5 phr may adversely affect the resolution. Depending on the combination of the other components in the resist composition, the organic acid derivative and fluorinated alcohol may be omitted.

Dissolution Inhibitor

In one preferred embodiment, the resist composition further contains (G) a dissolution inhibitor, that is, a compound with a weight average molecular weight of up to 3,000 which changes its solubility in an alkaline developer under the action of an acid. Typically, a compound obtained by substituting acid labile substituents for some or all hydrogen atoms of hydroxyl groups on a phenol or carboxylic acid derivative having a low molecular weight of up to 2,500 or fluorinated alcohol is added as the dissolution inhibitor.

Examples of the phenol or carboxylic acid derivative having a weight average molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, thymolphthalein, cholic acid, deoxycholic acid, and lithocholic acid. Examples of the fluorinated alcohol include compounds terminated with 1,1,1,3,3,3-hexafluoro-2-propanol as described in JP-A 2009-080474. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2''-tetrahydropyranyloxy))propane, 2,2-bis(4'-(2''-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1''-ethoxyethoxy)phenyl)propane, 2,2-bis(4'-(1''-ethoxypropyloxy)phenyl)propane, tert-butyl 4,4-bis(4'-(2''-tetrahydropyranyloxy)phenyl)valerate, tert-butyl 4,4-bis(4'-(2''-tetrahydrofuranyloxy)phenyl)valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1''-ethoxyethoxy)phenyl)valerate, tert-butyl 4,4-bis(4'-(1''-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2''-tetrahydropyranyloxy)phenyl)ethane, 1,1,2-tris(4'-(2''-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'-ethoxypropyloxy)phenyl)ethane, tert-butyl cholate, tert-butyl deoxycholate, and tert-butyl lithocholate. The compounds described in JP-A 2003-107706 are also useful.

In the resist composition, an appropriate amount of the dissolution inhibitor (G) is up to 20 parts, and especially up to 15 parts by weight per 100 parts by weight of the base resin. With more than 20 phr of the dissolution inhibitor, the resist composition becomes less heat resistant because of an increased content of monomer components.

Component C'

The base resin used in the negative working resist composition is (C') a base resin which is normally alkali soluble, but becomes substantially alkali insoluble under the action of a crosslinker. It is preferably a precursor resin which will be substituted with acid labile groups to form the base resin (C).

Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methyl-styrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer (to be protected with acid labile groups). Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as tert-butoxycarbonyl and relatively acid-undecomposable substituent groups such as tert-butyl and tert-butoxycarbonylmethyl.

In the resist composition, the resin (C') is blended in any desired amount, preferably of 65 to 99 parts by weight, especially 65 to 98 parts by weight among 100 parts by weight of the total solids.

Crosslinker

Formulated in the negative resist composition is an acid crosslinker (H) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker is, though not limited thereto, 1 to 20 parts, and especially 5 to 15 parts by weight per 100 parts by weight of the base resin. The crosslinkers may be used alone or in admixture of two or more.

Surfactant

To the chemically amplified resist composition may be added (S) a surfactant. Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (DIC Corp.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, KH-10, KH-20, KH-30 and KH-40 (Asahi Glass Co., Ltd.), and Surfynol E1004 (Nissin Chemical Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Partially fluorinated oxetane ring-opened polymers having the structural formula (surf-1) are also useful.

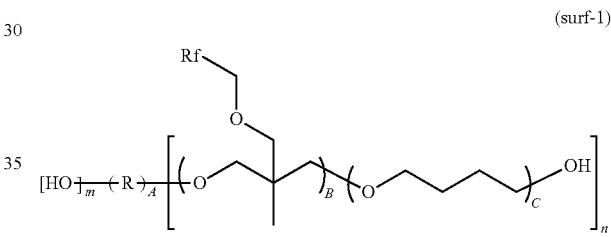

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

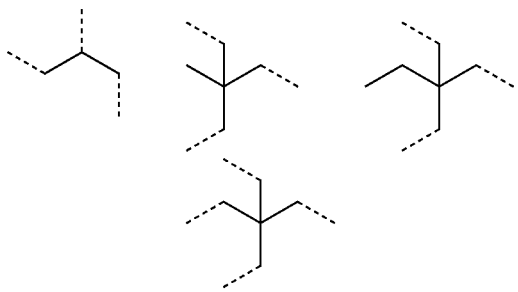

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20 and KH-30, and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage. Examples of the polymeric surfactant are described in JP-A 2007-297590, JP-A 2008-88343, JP-A 2008-111103 (U.S. Pat. No. 7,537,880), and JP-A 2008-122932 (US 2008090172). In the resist composition, the polymeric surfactant is preferably formulated in an amount of 0.001 to 20 parts, and more preferably 0.01 to 10 parts by weight, per 100 parts by to weight of the base resin.

In the chemically amplified resist composition, UV absorbers may be added. Those UV absorbers described in JP-A 11-190904 are useful, but the invention is not limited thereto. Exemplary UV absorbers are diaryl sulfoxide derivatives such as bis(4-hydroxyphenyl) sulfoxide, bis(4-tert-butoxyphenyl) sulfoxide, bis(4-tert-butoxycarbonyloxyphenyl) sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

The UV absorber may or may not be added to the resist composition depending on the type of resist composition. An appropriate amount of UV absorber, if added, is 0 to 10 parts, more preferably 0.5 to 10 parts, most preferably 1 to 5 parts by weight, per 100 parts by weight of the base resin.

In a further aspect, the invention provides a process for forming a pattern using the resist composition. Any well-known lithography may be employed in forming a pattern from the resist composition. For example, the composition is applied onto a substrate for integrated circuitry fabrication (e.g., Si, $SiO_2$, SiN, SiON, TiN, WSi, BPSG, SOG, organic antireflective coating, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.05 to 2.0 μm thick. A patterning mask having the desired pattern is then placed over the resist film, and the film exposed through the mask to an electron beam or to high-energy radiation such as deep-UV, excimer laser or x-ray in a dose of 1 to 200 $mJ/cm^2$, and preferably 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective film which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or electron beam. The desired pattern may not be obtainable outside the upper and lower limits of the above range.

The water-insoluble protective film which is used in the immersion lithography is to prevent the resist coating from being leached and to improve water slippage at the coating surface and is generally divided into two types. The first type is an organic solvent-strippable protective film which must be stripped, prior to alkaline development, with an organic solvent in which the resist coating is not dissolvable. The second type is an alkali-soluble protective film which is soluble in an alkaline developer so that it can be removed simultaneously with the removal of solubilized areas of the resist coating. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist coating is formed, a step of rinsing with pure water (post-soaking) may be introduced to extract the acid generator or the like from the coating surface or wash away particles. After exposure, a step of rinsing (post-soaking) may be introduced to remove any water remaining on the coating after exposure.

EXAMPLE

Examples and Comparative Examples are given below by way of illustration and not by way of limitation. A weight average molecular weight (Mw) and number average molecular weight (Mn) are measured by gel permeation chromatography (GPC) versus polystyrene standards. Mw/Mn designates a dispersity index or molecular weight distribution.

Synthesis Example 1

Synthesis of 4-fluorophenyldiphenylsulfonium chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was allowed to mature for 30 minutes at the temperature. Then, a Grignard reagent which had been prepared from 14.6 g (0.6 mole) of metallic magnesium, 78.3 g (0.6 mole) of 4-fluoro-chlorobenzene and 180 g of tetrahydrofuran (THF) was added dropwise at a temperature below 20° C. The reaction solution was allowed to mature for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of 4-fluorophenyldiphenylsulfonium chloride. The compound in aqueous solution form was used in the subsequent reaction without further isolation.

Synthesis Example 2

Synthesis of sodium 1,1,3,3,3-pentafluoro-2-hydroxy-propanesulfonate

Ester hydrolysis reaction was effected using sodium 1,1,3,3,3-pentafluoro-2-(pivaloyloxy)propanesulfonate, which was prepared according to the formulation described in JP-A 2007-145797, and a sodium hydroxide aqueous solution in methanol. After the completion of reaction, hydrochloric acid was added to turn the reaction system from neutral to weakly acidic. The aqueous solution was directly used in the subsequent reaction.

Synthesis Example 3

Synthesis of 4-fluorophenyldiphenylsulfonium 1,1,3,3,3-pentafluoro-2-hydroxypropanesulfonate An amount (0.2 mole) of the 4-fluorophenyldiphenyl-sulfonium chloride aqueous solution in Synthesis Example 1 was combined with an amount (0.2 mole) of the sodium 1,1,3,3,3-pentafluoro-2-hydroxypropanesulfonate aqueous solution in Synthesis Example 2, followed by twice extraction with 500 g of dichloromethane. Through the steps of washing the organic layer with water, distilling off the solvent in vacuum, adding isopropyl ether for crystallization, filtration and drying, the target compound was obtained. White crystals, 71.5 g, yield 70% (based on diphenyl sulfoxide).

Synthesis Example 4

Synthesis of 4-(1,1,3,3,3-pentafluoro-2-sulfonatopropan-2-yloxy)phenyldiphenylsulfonium [PAG-1]

Sodium hydride, 0.2 g (5 mmol), was dissolved or suspended in 10 g of THF, to which 10 g of a THF solution containing 2.6 g (5 mmol) of 4-fluorophenyldiphenylsulfonium 1,1,3,3,3-pentafluoro-2-hydroxypropanesulfonate in Synthesis Example 3 was added, followed by stirring at room temperature. Thereafter, 40 g of methylene chloride and 30 g of water were added to the solution, from which the organic layer was taken out. The organic layer was washed with water, and methyl isobutyl ketone was added thereto. By concentration, the solvent and a minor amount of water were removed. A solid precipitating out during concentration was washed with diisopropyl ether and dried, obtaining the target compound. White crystals, 2.3 g, yield 86%.

Figure 2:
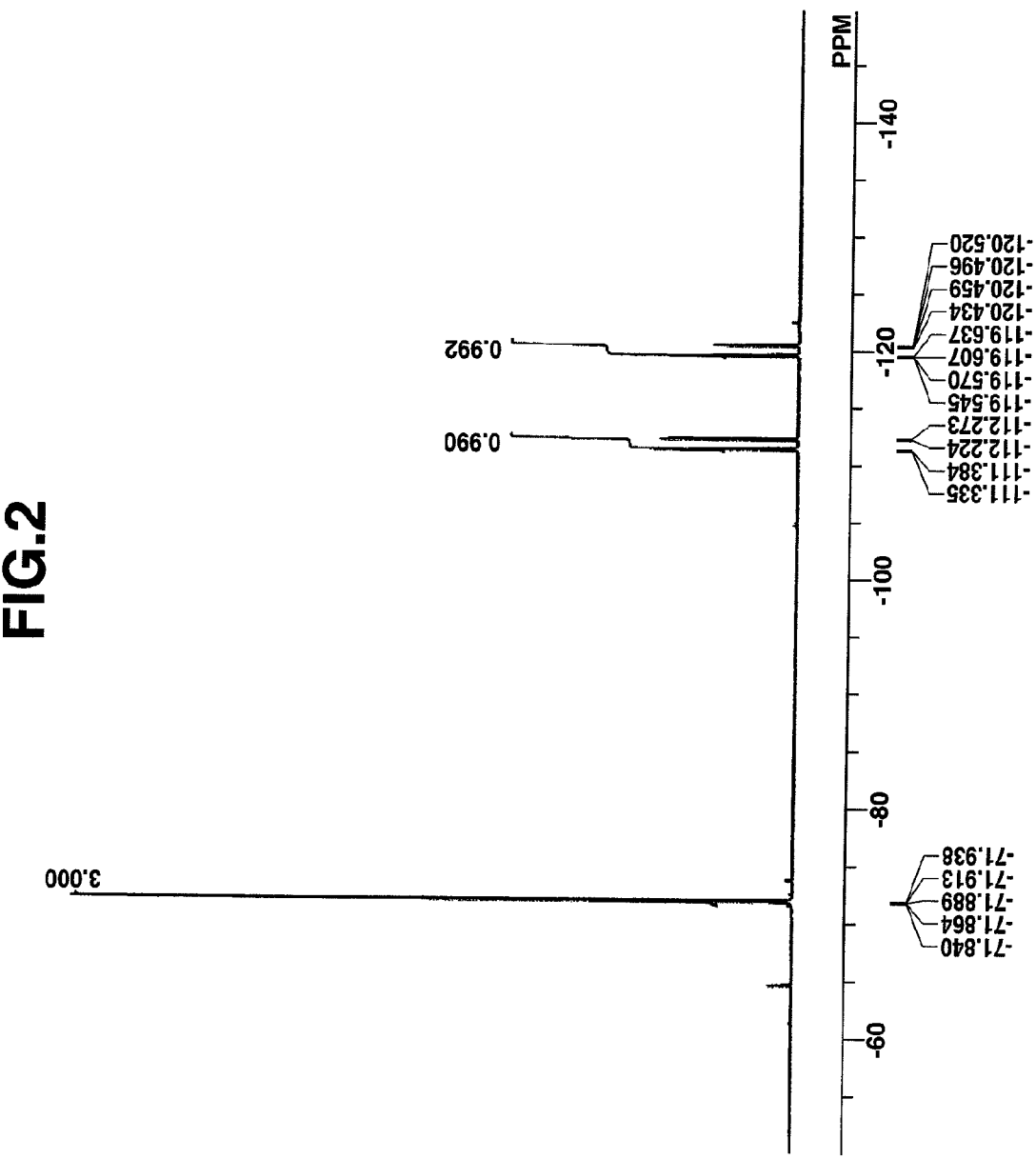
FIG. 2 is a diagram showing the $^{19}$F-NMR/DMSO-$d_6$ spectrum of PAG-1 in Synthesis Example 4.

The compound was analyzed by spectroscopy. The nuclear magnetic resonance spectra, $^1$H-NMR and $^{19}$F-NMR/DMSO-$d_6$ are shown in FIGS. 1 and 2. Note that in $^1$H-NMR, traces of residual solvents (diisopropyl ether, methyl isobutyl ketone, THF, water) were observed. The data of liquid chromatography/mass spectrometry are also shown.

IR spectrum (KBr, cm$^{-1}$)
3444, 1587, 1492, 1477, 1448, 1247, 1186, 1162, 1118, 1070, 997, 883, 836, 750, 684, 642, 524 cm$^{-1}$
LC-MS
Positive [M+H]$^+$ 491

Synthesis Example 5

Synthesis of benzyltrimethylammonium 1,1-difluoro-2-hydroxyethanesulfonate

Sodium 1,1-difluoro-2-(pivaloyloxy)ethanesulfonate, which was prepared according to the formulation described in JP-A 2009-007327, and benzyltrimethylammonium chloride were stirred in dichloromethane/water, whereby benzyltrimethyl-ammonium 1,1-difluoro-2-(pivaloyloxy)ethanesulfonate was extracted into the organic layer. The solvent was distilled off in vacuum. The concentrate was dissolved in methanol, to which 50% sodium hydroxide aqueous solution was added to effect ester hydrolysis. Aqueous hydrochloric acid was added to the reaction system until neutral, after which methanol was distilled off in vacuum. Isopropyl ether was added to the residue for crystallization. Crude crystals, which contained a minor amount of sodium chloride, were directly used in the subsequent step.

Synthesis Example 6

Synthesis of 4-fluorophenyldiphenylsulfonium 4-toluene-sulfonate

The 4-fluorophenyldiphenylsulfonium chloride aqueous solution in Synthesis Example 1 was combined with 4-toluenesulfonic acid monohydrate, followed by extraction with dichloromethane. The organic layer was washed with water, after which the solvent was distilled off in vacuum. Isopropyl ether was added to the residue for crystallization. Filtration and drying yielded the target compound.

Synthesis Example 7

Synthesis of 4-(1,1-difluoro-1-sulfonatoethoxy)phenyl-diphenylsulfonium [PAG-2]

In N,N-dimethylformamide was dissolved a mixture of the benzyltrimethylammonium 1,1-difluoro-2-hydroxyethanesulfonate in Synthesis Example 5 and the 4-fluorophenyldiphenylsulfonium 4-toluenesulfonate in Synthesis Example 6 in a molar ratio of 1:1. Potassium carbonate was added to the solution, which was heated and stirred at 90° C. Water and dichloromethane were added to the reaction solution, from which the organic layer was taken out and concentrated. The residue was purified by silica gel column chromatography. Isopropyl ether was added thereto for crystallization, obtaining the target compound. White crystals, 2.0 g, yield 47%.

Figure 3:
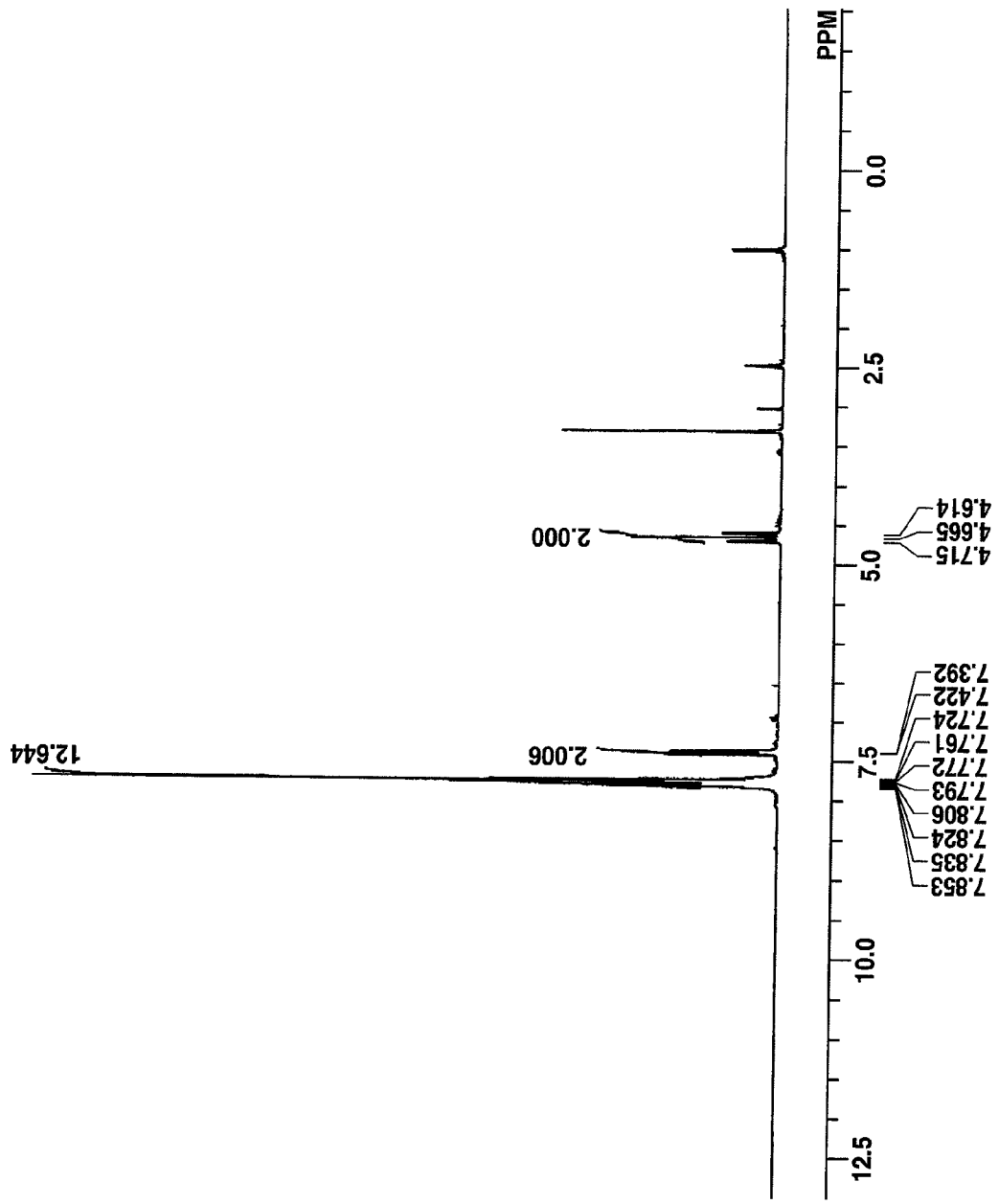
FIG. 3 is a diagram showing the $^1$H-NMR/DMSO-$d_6$ spectrum of PAG-2 in Synthesis Example 7.
Figure 4:
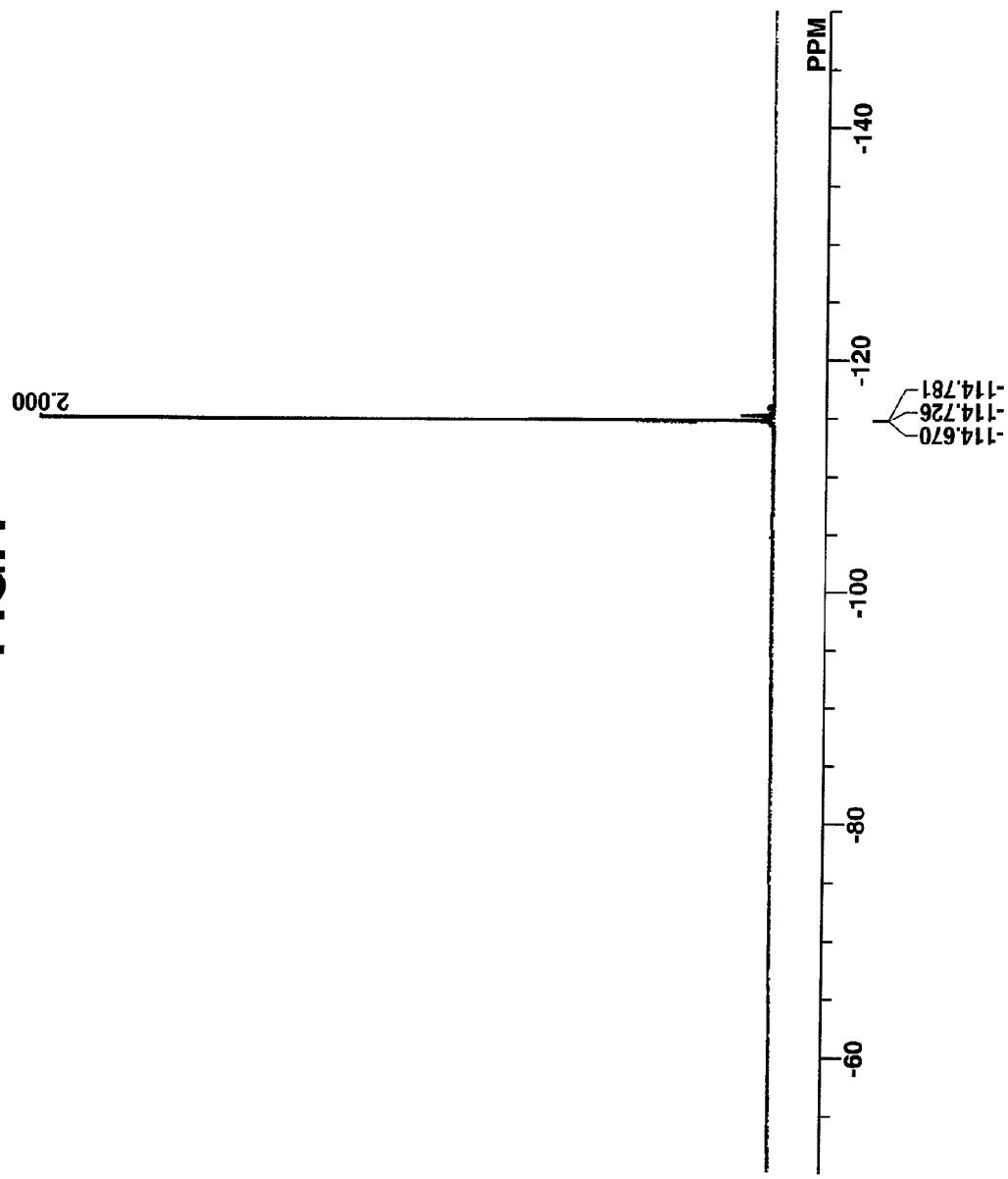
FIG. 4 is a diagram showing the $^{19}$F-NMR/DMSO-$d_6$ spectrum of PAG-2 in Synthesis Example 7.

The compound was analyzed by spectroscopy. The nuclear magnetic resonance spectra, $^1$H-NMR and $^{19}$F-NMR/DMSO-$d_6$ are shown in FIGS. 3 and 4. Note that in $^1$H-NMR, traces of residual solvents (diisopropyl ether, water) were observed. The data of liquid chromatography/mass spectrometry are also shown.

IR spectrum (KBr, cm$^{-1}$)

3443, 1587, 1491, 1477, 1448, 1246, 1186, 1162, 1119, 1070, 997, 884, 836, 749, 684, 642, 524 cm$^{-1}$

LC-MS

Positive [M+H]$^+$423

Polymers were synthesized according to the following formulation.

Synthesis Example 8-1

Synthesis of Polymer 1

A flask under a nitrogen blanket was charged with 168.6 g of 2-ethyladamantan-2-yl methacrylate, 85.5 g of 3-hydroxy-1-adamantyl methacrylate, 172.1 g of 2-oxotetrahydrofuran-3-yl methacrylate, and 510 g of propylene glycol methyl ether acetate (PGMEA) to form a monomer solution. An initiator solution was prepared by combining 14.86 g of 2,2'-azobisisobutyronitrile, 2.6 g of 2-mercaptoethanol, and 127 g of PGMEA. Another flask under a nitrogen blanket was charged with 292 g of PGMEA, which was heated to 80° C. with stirring. To the other flask, the monomer solution and the initiator solution were simultaneously added dropwise over 4 hours. After the completion of dropwise addition, the polymerization solution was stirred for a further 2 hours while maintaining the temperature of 80° C. Thereafter the polymerization solution was cooled to room temperature, and with vigorous stirring, added dropwise to 12 kg of methanol. A precipitating copolymer was filtered. The copolymer was washed twice with 3 kg of methanol and vacuum dried at 50° C. for 20 hours, obtaining 384 g of the copolymer in white powder form. On $^{13}$C-NMR analysis, the copolymer was found to consist of 33/18/49 mol % of the monomers in the described order. The copolymer had a Mw of 6,000.

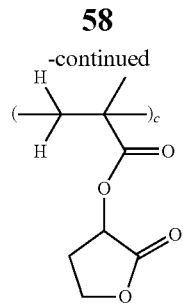

($a = 0.33, b = 0.18, c = 0.49$)

Synthesis Examples 8-2 to 8-18

Synthesis of Polymers 2 to 18

Polymers 2 to 18 as shown in Table 1 were prepared by the same procedure as Synthesis Example 8-1 except that the type and proportion of monomers were changed. The structure of the units in Table 1 is shown in Tables 2 to 5. Note that in Table 1, the ratio of units incorporated is expressed in a molar ratio.

Synthesis Example 8-19

Synthesis of Polymer 19

In a 300-mL dropping cylinder under a nitrogen blanket, 58.3 g of acetoxystyrene, 6.7 g of indene, 35.0 g of tert-butoxycarbonylstyrene, 10.9 g of dimethyl 2,2'-azobis(2-methylpropionate) (V-601 by Wako Pure Chemical Industries, Ltd.), and 140 g of toluene were fed to form a monomer solution. A 500-mL flask under a nitrogen blanket was charged with 46 g of toluene and heated at 80° C., after which the monomer solution was added dropwise over 4 hours. After the completion of dropwise addition, the polymerization solution was stirred for 20 hours while maintaining the temperature of 80° C. It was then cooled to room temperature. The polymerization solution was added dropwise to 1,860 g of hexane, after which the precipitated copolymer was filtered. The copolymer was washed twice with 300 g of hexane before it was used in the subsequent step.

In a nitrogen atmosphere, the copolymer was dissolved in 240 g of THF and 240 g of methanol. The solution was combined with 63 g of triethylamine in 11 g of water. The reaction solution was stirred for a time, then concentrated, and neutralized with acetic acid and pyridine. The concentrate was dissolved in 100 g of acetone and poured into 2,500 g of water for precipitation. By filtration and drying, 80.0 g of a white polymer was obtained. It was analyzed by $^{13}$C- and $^1$H-NMR and GPC, with the analytical data shown below.

Polymer 19
Mw = 5,000, Mw/Mn = 1.56

Synthesis Examples 8-20 to 27, 34 to 36

Synthesis of Polymers 20 to 27, 34 to 36

Polymers shown in Table 1 were prepared by the same procedure as Synthesis Example 8-1 except that the type and proportion of monomers were changed. The structure of the units in Table 1 is shown in Tables 2 to 5. Note that in Table 1, the ratio of units incorporated is expressed in a molar ratio.

Synthesis Example 8-28

Synthesis of Polymer 28

The target polymer was obtained by preparing polyhydroxystyrene and reacting it with 1-chloro-1-methoxy-2-methylpropane under basic conditions in accordance with the anionic polymerization method described in JP 3981830.

Synthesis Examples 8-29 to 33

Synthesis of Polymers 29 to 33

Polymers composed of hydroxystyrene/acetoxystyrene units, hydroxystyrene/indene units or hydroxystyrene/acenaphthylene units were prepared by the same procedure as Synthesis Example 8-1 except that the type and proportion of monomers were changed. The polymers were further reacted with 1-chloro-1-methoxy-2-methylpropane or 1-chloro-1-(tricyclododecanyloxy)-2-methylpropane under basic conditions, yielding the target polymers.

With respect to the preparation of polyhydroxystyrene derivatives, reference should be made to JP-A 2001-272785, JP-A 2002-062652, JP-A 2002-202610, JP-A 2002-234910, JP-A 2003-131384, JP-A 2005-008766, and JP-A 2008-095009.

TABLE 1

|  |  | Resin | Unit 1 (incorporation ratio) | Unit 2 (incorporation ratio) | Unit 3 (incorporation ratio) | Unit 4 (incorporation ratio) |
|---|---|---|---|---|---|---|
| Synthesis Example | 8-1 | Polymer 1 | A-3M(0.33) | B-1M(0.18) | B-6M(0.49) | — |
|  | 8-2 | Polymer 2 | A-6M(0.25) | B-1M(0.25) | B-3M(0.40) | C-3M(0.10) |
|  | 8-3 | Polymer 3 | A-1M(0.25) | B-1M(0.25) | B-3M(0.40) | C-3M(0.10) |
|  | 8-4 | Polymer 4 | A-5M(0.30) | B-1M(0.25) | B-3M(0.35) | C-2M(0.10) |
|  | 8-5 | Polymer 5 | A-2M(0.40) | B-1M(0.25) | B-3M(0.35) | — |
|  | 8-6 | Polymer 6 | A-1M(0.25) | B-1M(0.25) | B-3M(0.40) | A-2M(0.10) |
|  | 8-7 | Polymer 7 | A-1M(0.30) | B-1M(0.15) | B-3M(0.45) | C-4M(0.10) |
|  | 8-8 | Polymer 8 | A-5M(0.25) | B-1M(0.25) | B-3M(0.40) | C-1M(0.10) |
|  | 8-9 | Polymer 9 | A-3M(0.35) | B-1M(0.35) | B-4M(0.30) | — |
|  | 8-10 | Polymer 10 | A-3M(0.35) | B-1M(0.35) | B-7M(0.30) | — |
|  | 8-11 | Polymer 11 | A-3M(0.30) | B-1M(0.26) | B-6M(0.34) | B-8M(0.10) |
|  | 8-12 | Polymer 12 | A-1M(0.25) | B-1M(0.25) | B-9M(0.40) | B-8M(0.10) |
|  | 8-13 | Polymer 13 | A-1M(0.25) | B-1M(0.25) | B-3M(0.40) | C-1M(0.10) |
|  | 8-14 | Polymer 14 | A-4M(0.30) | B-1M(0.25) | B-3M(0.45) | — |
|  | 8-15 | Polymer 15 | A-1M(0.30) | B-2M(0.35) | B-6M(0.35) | — |
|  | 8-16 | Polymer 16 | A-1M(0.30) | B-1M(0.35) | B-3M(0.35) | — |
|  | 8-17 | Polymer 17 | A-1M(0.35) | B-1M(0.25) | B-5M(0.40) | — |
|  | 8-18 | Polymer 18 | A-1M(0.20) | B-1M(0.25) | B-3M(0.35) | A-5M(0.20) |
|  | 8-19 | Polymer 19 | D-1(0.62) | D-9(0.10) | D-7(0.28) | — |
|  | 8-20 | Polymer 20 | D-1(0.62) | D-10(0.10) | D-7(0.28) | — |
|  | 8-21 | Polymer 21 | D-1(0.62) | D-9(0.10) | D-5(0.28) | — |
|  | 8-22 | Polymer 22 | D-1(0.62) | D-10(0.10) | D-5(0.28) | — |
|  | 8-23 | Polymer 23 | D-1(0.62) | D-9(0.10) | D-3(0.28) | — |
|  | 8-24 | Polymer 24 | D-1(0.62) | D-10(0.10) | D-3(0.28) | — |
|  | 8-25 | Polymer 25 | D-1(0.70) | D-5(0.20) | D-7(0.10) | — |
|  | 8-26 | Polymer 26 | D-1(0.72) | D-5(0.28) | — | — |
|  | 8-27 | Polymer 27 | D-1(0.72) | D-7(0.28) | — | — |
|  | 8-28 | Polymer 28 | D-1(0.70) | D-4(0.30) | — | — |
|  | 8-29 | Polymer 29 | D-1(0.70) | D-2(0.10) | D-4(0.20) | — |
|  | 8-30 | Polymer 30 | D-1(0.70) | D-9(0.10) | D-4(0.20) | — |
|  | 8-31 | Polymer 31 | D-1(0.70) | D-10(0.10) | D-4(0.20) | — |
|  | 8-32 | Polymer 32 | D-1(0.78) | D-9(0.10) | D-6(0.12) | — |
|  | 8-33 | Polymer 33 | D-1(0.78) | D-10(0.10) | D-6(0.12) | — |
|  | 8-34 | Polymer 34 | D-1(0.75) | D-9(0.18) | D-2(0.07) | — |
|  | 8-35 | Polymer 35 | D-1(0.76) | D-9(0.12) | D-8(0.12) | — |
|  | 8-36 | Polymer 36 | D-1(0.73) | D-10(0.11) | D-8(0.16) | — |

TABLE 2

A-1M (R = CH₃), A-1A (R = H); A-2M (R = CH₃), A-2A (R = H); A-3M (R = CH₃), A-3A (R = H); A-4M (R = CH₃), A-4A (R = H); A-5M (R = CH₃), A-5A (R = H); A-6M (R = CH₃), A-6A (R = H)

TABLE 3

B-1M (R = CH₃), B-1A (R = H); B-2M (R = CH₃), B-2A (R = H); B-3M (R = CH₃), B-3A (R = H); B-4M (R = CH₃), B-4A (R = H); B-5M (R = CH₃), B-5A (R = H); B-6M (R = CH₃), B-6A (R = H); B-7M (R = CH₃), B-7A (R = H); B-8M (R = CH₃), B-8A (R = H); B-9M (R = CH₃), B-9A (R = H)

TABLE 3-continued
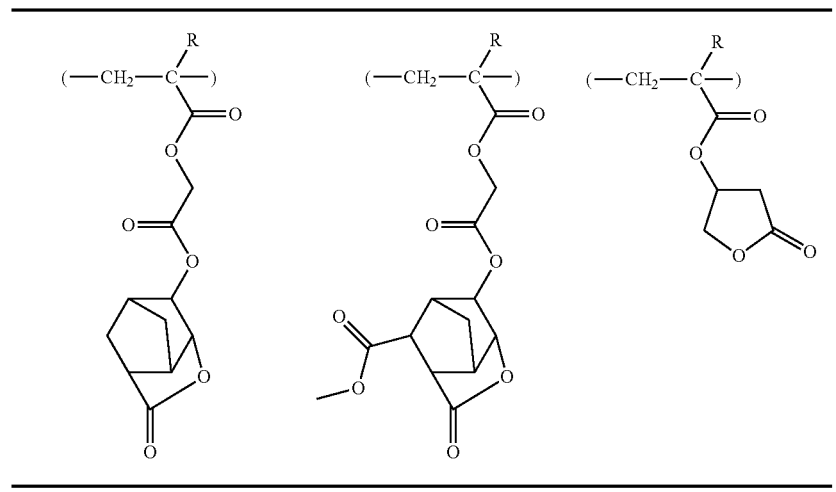
TABLE 4
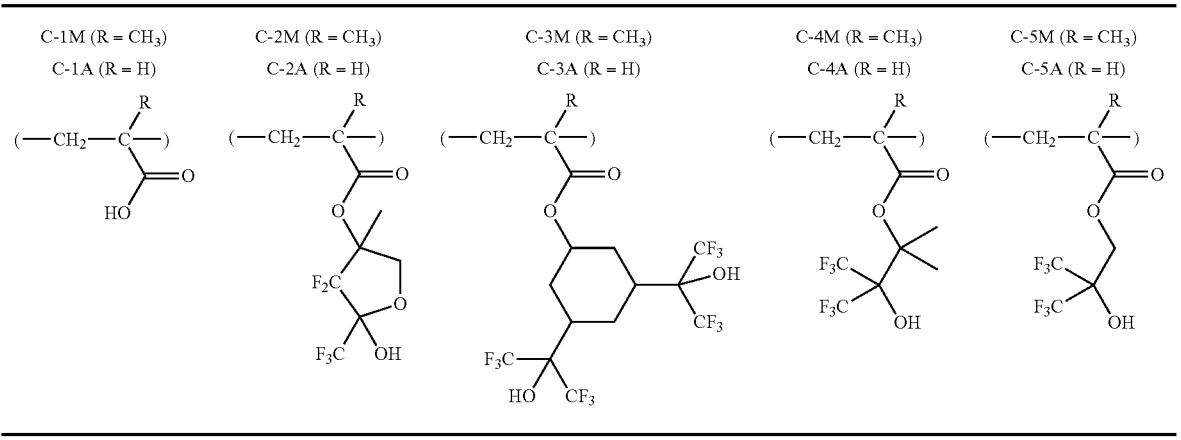
C-1M (R = CH₃)  C-2M (R = CH₃)  C-3M (R = CH₃)  C-4M (R = CH₃)  C-5M (R = CH₃)
C-1A (R = H)    C-2A (R = H)    C-3A (R = H)    C-4A (R = H)    C-5A (R = H)
TABLE 5
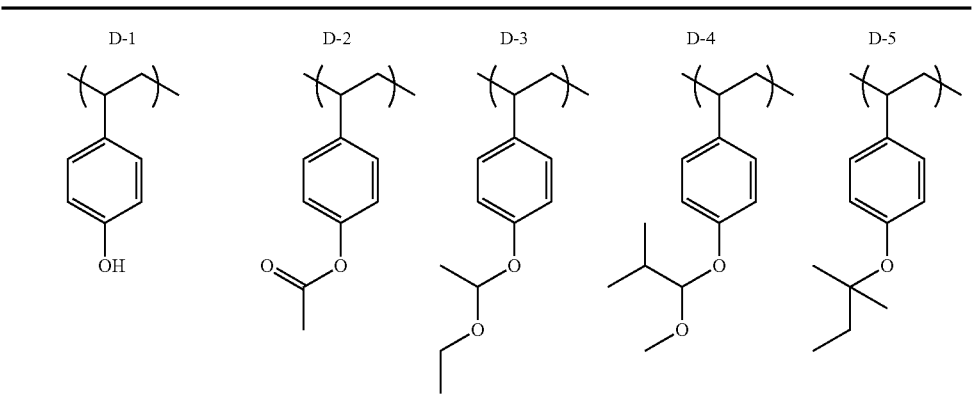
D-1   D-2   D-3   D-4   D-5

TABLE 5-continued
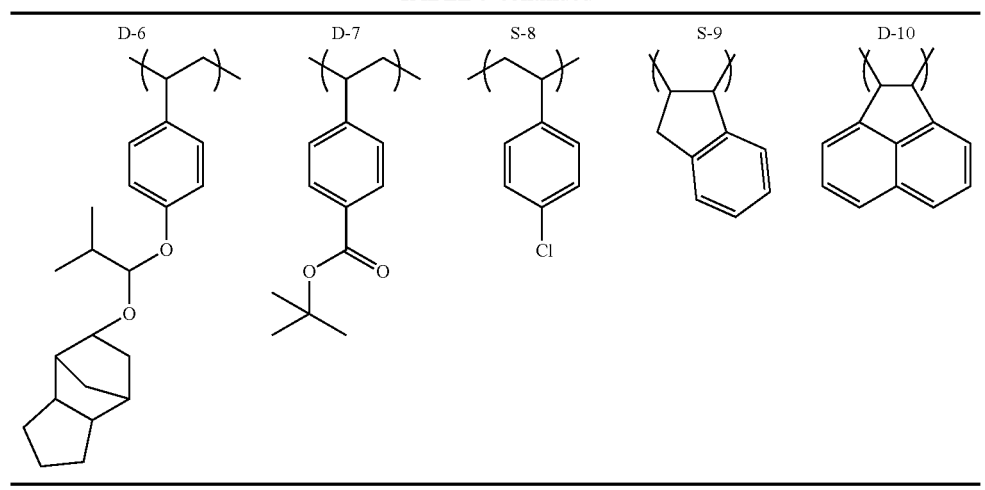
Besides, Polymers 37 to 41 of the structures shown below were prepared by the known technique.
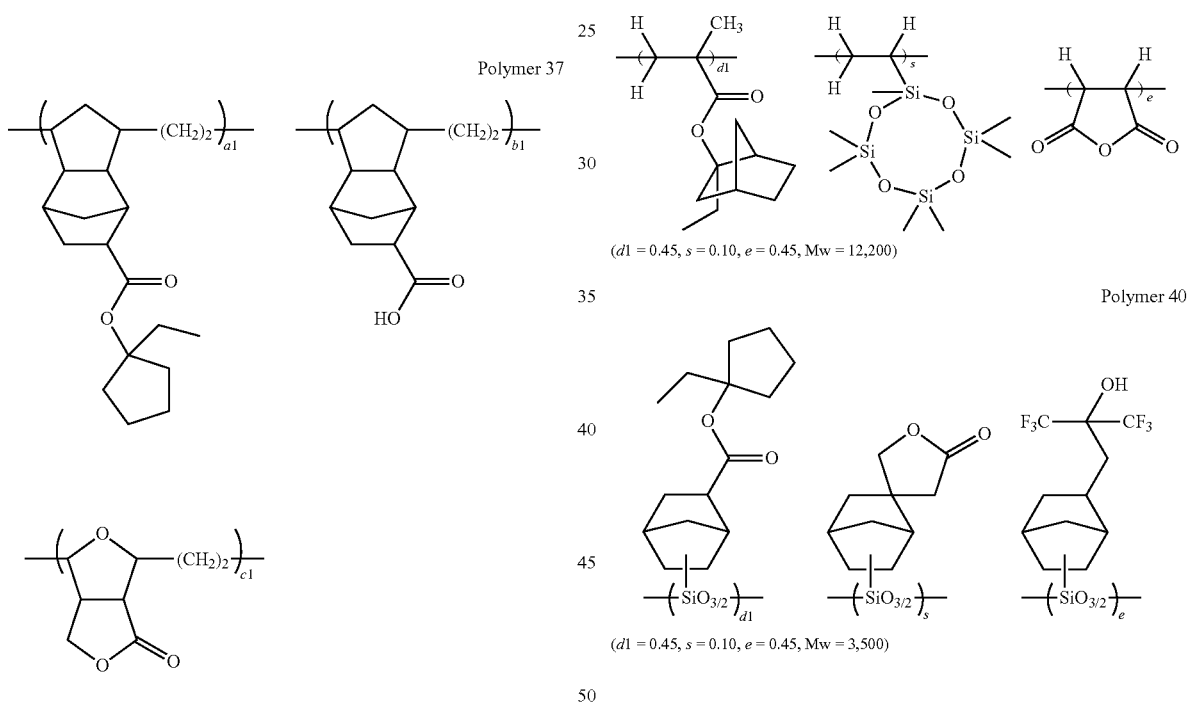
Polymer 37
($a1 = 0.35$, $b1 = 0.15$, $c1 = 0.50$, Mw = 8,100)
Polymer 38
($d1 = 0.40$, $s = 0.20$, $e = 0.40$, Mw = 10,200)
Polymer 39
($d1 = 0.45$, $s = 0.10$, $e = 0.45$, Mw = 12,200)
Polymer 40
($d1 = 0.45$, $s = 0.10$, $e = 0.45$, Mw = 3,500)
Polymer 41
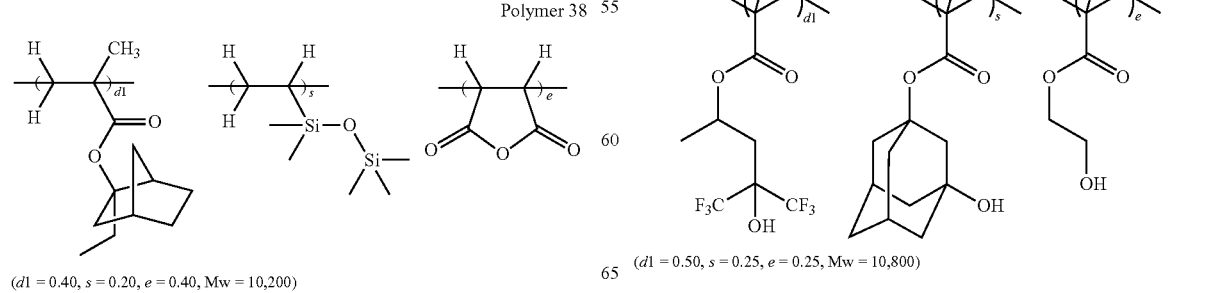
($d1 = 0.50$, $s = 0.25$, $e = 0.25$, Mw = 10,800)

Examples 1 to 42 and Comparative Examples 1 to 9

Preparation of Resist Compositions

Resist compositions were prepared by dissolving each of the photoacid generators, each of the polymers, both synthesized above, and a quencher in a solvent in accordance with the recipe shown in Tables 6 and 7. They were filtered through a Teflon filter having a pore size of 0.2 μm, giving resist solutions. Note that the solvent contained 0.01 wt % of a surfactant.

In Tables 6 and 7, the solvents, quenchers, photoacid generators (in Comparative Examples), and acid crosslinker are shown below.
PAG-1, PAG-2: shown above
P-01 to P-41: Polymers 1 to 41
PGMEA: propylene glycol monomethyl ether acetate
CyHO: cyclohexanone
EL: ethyl lactate
Base-1: 2-morpholinoethyl dodecanoate
Base-2: tris[2-(methoxymethoxy)ethyl]amine N-oxide
Base-3: tris[2-(methoxymethoxy)ethyl]amine
Base-4: p-dibutylaminobenzoic acid
PAG-Y: triphenylsulfonium perfluoro-1-butanesulfonate
PAG-Z: triphenylsulfonium 2,4,6-triisopropylbenzene-sulfonate
TMGU: 1,3,4,6-tetramethoxymethylglycoluril Surfactant: 3-methyl-3-(2,2,2-trifluoroethoxymethyl)oxetane/tetrahydrofuran/2,2-dimethyl-1,3-propane diol copolymer of the structural formula below (Omnova Solutions, Inc.)

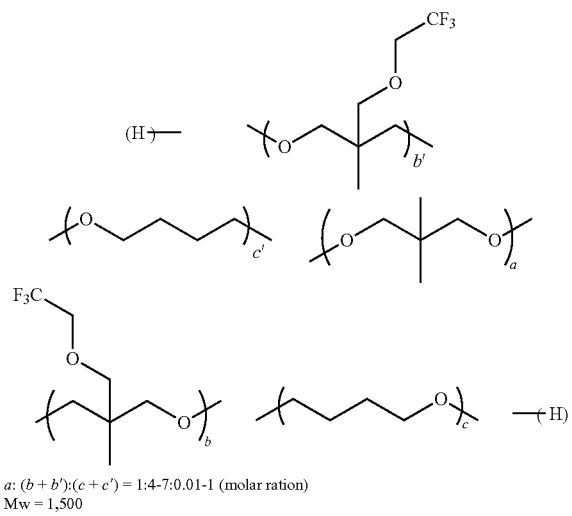

$a : (b + b') : (c + c') = 1 : 4\text{-}7 : 0.01\text{-}1$ (molar ration)
Mw = 1,500

TABLE 6

| | | Resist | Resin (pbw) | Acid generator (pbw) | Additive (pbw) | Solvent 1 (pbw) | Solvent 2 (pbw) |
|---|---|---|---|---|---|---|---|
| Example | 1 | R-01 | P-01(80) | PAG-1(9.5) | Base-1(1.97) | PGMEA(1,400) | CyHO(600) |
| | 2 | R-02 | P-01(80) | PAG-2(8.2) | Base-1(1.97) | PGMEA(1,400) | CyHO(600) |
| | 3 | R-03 | P-01(80) | PAG-1(4.8) PAG-2(4.1) | Base-1(1.97) | PGMEA(1,400) | CyHO(600) |
| | 4 | R-04 | P-02(80) | PAG-1(9.5) | Base-1(1.97) | PGMEA(1,400) | CyHO(600) |
| | 5 | R-05 | P-03(80) | PAG-1(9.5) | Base-1(1.97) | PGMEA(1,400) | CyHO(600) |
| | 6 | R-06 | P-04(80) | PAG-1(9.5) | Base-1(1.97) | PGMEA(1,400) | CyHO(600) |
| | 7 | R-07 | P-05(80) | PAG-1(9.5) | Base-1(1.97) | PGMEA(1,400) | CyHO(600) |
| | 8 | R-08 | P-06(80) | PAG-1(9.5) | Base-1(1.97) | PGMEA(1,400) | CyHO(600) |
| | 9 | R-09 | P-07(80) | PAG-1(9.5) | Base-1(1.97) | PGMEA(1,400) | CyHO(600) |
| | 10 | R-10 | P-08(80) | PAG-1(9.5) | Base-1(1.97) | PGMEA(1,400) | CyHO(600) |
| | 11 | R-11 | P-09(80) | PAG-1(9.5) | Base-1(1.97) | PGMEA(1,400) | CyHO(600) |
| | 12 | R-12 | P-10(80) | PAG-1(9.5) | Base-1(1.97) | PGMEA(1,400) | CyHO(600) |
| | 13 | R-13 | P-11(80) | PAG-1(9.5) | Base-1(1.97) | PGMEA(1,400) | CyHO(600) |
| | 14 | R-14 | P-12(80) | PAG-1(9.5) | Base-1(1.97) | PGMEA(1,400) | CyHO(600) |
| | 15 | R-15 | P-13(80) | PAG-1(9.5) | Base-1(1.97) | PGMEA(1,400) | CyHO(600) |
| | 16 | R-16 | P-14(80) | PAG-1(9.5) | Base-1(1.97) | PGMEA(1,400) | CyHO(600) |
| | 17 | R-17 | P-15(80) | PAG-1(9.5) | Base-1(1.97) | PGMEA(1,400) | CyHO(600) |
| | 18 | R-18 | P-16(80) | PAG-1(9.5) | Base-1(1.97) | PGMEA(1,400) | CyHO(600) |
| | 19 | R-19 | P-17(80) | PAG-1(9.5) | Base-1(1.97) | PGMEA(1,400) | CyHO(600) |
| | 20 | R-20 | P-18(80) | PAG-1(9.5) | Base-1(1.97) | PGMEA(1,400) | CyHO(600) |
| | 21 | R-21 | P-03(40) P-36(40) | PAG-1(9.5) | Base-1(1.97) | PGMEA(1,400) | CyHO(600) |
| | 22 | R-22 | P-05(40) P-37(40) | PAG-1(9.5) | Base-1(1.97) | PGMEA(1,400) | CyHO(600) |
| | 23 | R-23 | P-38(80) | PAG-1(9.5) | Base-1(1.97) | PGMEA(1,400) | CyHO(600) |
| | 24 | R-24 | P-39(80) | PAG-1(9.5) | Base-1(1.97) | PGMEA(1,400) | CyHO(600) |
| | 25 | R-25 | P-19(80) | PAG-1(8.0) | Base-2(0.85) | PGMEA(950) | EL(2,218) |
| | 26 | R-26 | P-20(80) | PAG-1(8.0) | Base-2(0.85) | PGMEA(950) | EL(2,218) |
| | 27 | R-27 | P-21(80) | PAG-1(8.0) | Base-2(0.85) | PGMEA(950) | EL(2,218) |
| | 28 | R-28 | P-22(80) | PAG-1(8.0) | Base-2(0.85) | PGMEA(950) | EL(2,218) |
| | 29 | R-29 | P-23(80) | PAG-1(8.0) | Base-2(0.85) | PGMEA(950) | EL(2,218) |
| | 30 | R-30 | P-24(80) | PAG-1(8.0) | Base-2(0.85) | PGMEA(950) | EL(2,218) |
| | 31 | R-31 | P-25(80) | PAG-1(8.0) | Base-2(0.85) | PGMEA(950) | EL(2,218) |
| | 32 | R-32 | P-26(80) | PAG-1(8.0) | Base-2(0.85) | PGMEA(950) | EL(2,218) |
| | 33 | R-33 | P-27(80) | PAG-1(8.0) | Base-2(0.85) | PGMEA(950) | EL(2,218) |
| | 34 | R-34 | P-28(80) | PAG-1(8.0) | Base-2(0.85) | PGMEA(950) | EL(2,218) |
| | 35 | R-35 | P-29(80) | PAG-1(8.0) | Base-2(0.85) | PGMEA(950) | EL(2,218) |
| | 36 | R-36 | P-30(80) | PAG-1(8.0) | Base-2(0.85) | PGMEA(950) | EL(2,218) |
| | 37 | R-37 | P-31(80) | PAG-1(8.0) | Base-2(0.85) | PGMEA(950) | EL(2,218) |
| | 38 | R-38 | P-32(80) | PAG-1(8.0) | Base-2(0.85) | PGMEA(950) | EL(2,218) |

TABLE 6-continued

| | Resist | Resin (pbw) | Acid generator (pbw) | Additive (pbw) | Solvent 1 (pbw) | Solvent 2 (pbw) |
|---|---|---|---|---|---|---|
| 39 | R-39 | P-33(80) | PAG-1(8.0) | Base-2(0.85) | PGMEA(950) | EL(2,218) |
| 40 | R-40 | P-34(80) | PAG-1(10.0) | Base-3(0.20) Base-4(0.10) TMGU(8.0) | PGMEA(950) | EL(2,218) |
| 41 | R-41 | P-35(80) | PAG-1(10.0) | Base-3(0.20) Base-4(0.10) TMGU(8.0) | PGMEA(950) | EL(2,218) |
| 42 | R-42 | P-36(80) | PAG-1(10.0) | Base-3(0.20) Base-4(0.10) TMGU(8.0) | PGMEA(950) | EL(2,218) |

TABLE 7

| | | Resist | Resin (pbw) | Acid generator (pbw) | Additive (pbw) | Solvent 1 (pbw) | Solvent 2 (pbw) |
|---|---|---|---|---|---|---|---|
| Comparative Example | 1 | R-101 | P-01(80) | PAG-Y(6.5) | Base-1(1.97) | PGMEA(1,400) | CyHO(600) |
| | 2 | R-102 | P-02(80) | PAG-Y(6.5) | Base-1(1.97) | PGMEA(1,400) | CyHO(600) |
| | 3 | R-103 | P-11(80) | PAG-Y(6.5) | Base-1(1.97) | PGMEA(1,400) | CyHO(600) |
| | 4 | R-104 | P-20(80) | PAG-Z(8.0) | Base-2(0.85) | PGMEA(950) | EL(2,218) |
| | 5 | R-105 | P-22(80) | PAG-Z(8.0) | Base-2(0.85) | PGMEA(950) | EL(2,218) |
| | 6 | R-106 | P-24(80) | PAG-Z(8.0) | Base-2(0.85) | PGMEA(950) | EL(2,218) |
| | 7 | R-107 | P-31(80) | PAG-Z(8.0) | Base-2(0.85) | PGMEA(950) | EL(2,218) |
| | 8 | R-108 | P-33(80) | PAG-Z(8.0) | Base-2(0.85) | PGMEA(950) | EL(2,218) |
| | 9 | R-109 | P-36(80) | PAG-Z(8.0) | Base-1(0.20) Base-2(0.10) TMGU(8.0) | PGMEA(950) | EL(2,218) |

Examples 43 to 66 and Comparative Examples 10 to 12

Evaluation of Resolution and Exposure Latitude on ArF Lithography

On a silicon substrate, an antireflective coating solution (ARC-29A, Nissan Chemical Co., Ltd.) was coated and baked at 200° C. for 60 seconds to form an ARC of 78 nm thick. Each of the positive resist compositions (R-01 to 24 and R-101 to 103) was spin coated on the ARC-coated silicon substrate and baked on a hot plate at 100° C. for 60 seconds, forming a resist film of 120 nm thick. The coated substrate was exposed by means of an ArF excimer laser scanner NSR-S307E (Nikon Corp., NA 0.85, dipole illumination, Cr mask), post-exposure baked (PEB) at a proper temperature as shown in Table 8 for 60 seconds, and developed with a 2.38 wt % tetramethylammonium hydroxide aqueous solution for 60 seconds.

The optimum exposure (Eop) was defined as the exposure dose (mJ/cm$^2$) which provided a 1:1 resolution at the top and bottom of a 65-nm grouped line-and-space pattern. For the evaluation of exposure latitude, an exposure dose tolerance which provided a pattern size of 65 nm±10% when the exposure dose was changed from the optimum was determined, and the tolerance value was divided by the optimum dose and expressed in percent. A greater value indicates a smaller performance change with a change of exposure dose, that is, better exposure latitude. The results are shown in Table 8.

TABLE 8

| | | Resist composition | PEB temp. (° C.) | Optimum exposure (mJ/cm$^2$) | Exposure latitude (%) |
|---|---|---|---|---|---|
| Example | 43 | R-01 | 105 | 60 | 16 |
| | 44 | R-02 | 105 | 62 | 15 |
| | 45 | R-03 | 105 | 60 | 15 |
| | 46 | R-04 | 110 | 55 | 16 |
| | 47 | R-05 | 100 | 60 | 17 |
| | 48 | R-06 | 110 | 58 | 18 |
| | 49 | R-07 | 120 | 55 | 15 |
| | 50 | R-08 | 130 | 60 | 14 |
| | 51 | R-09 | 110 | 60 | 16 |
| | 52 | R-10 | 105 | 62 | 16 |
| | 53 | R-11 | 120 | 60 | 15 |
| | 54 | R-12 | 115 | 55 | 17 |
| | 55 | R-13 | 105 | 60 | 17 |
| | 56 | R-14 | 90 | 58 | 17 |
| | 57 | R-15 | 90 | 55 | 17 |
| | 58 | R-16 | 110 | 62 | 16 |
| | 59 | R-17 | 125 | 60 | 15 |
| | 60 | R-18 | 100 | 55 | 17 |
| | 61 | R-19 | 110 | 60 | 17 |
| | 62 | R-20 | 110 | 58 | 15 |
| | 63 | R-21 | 110 | 55 | 15 |
| | 64 | R-22 | 130 | 62 | 14 |
| | 65 | R-23 | 100 | 58 | 14 |
| | 66 | R-24 | 100 | 60 | 14 |
| Comparative Example | 10 | R-101 | 105 | 24 | 5 |
| | 11 | R-102 | 110 | 23 | 6 |
| | 12 | R-103 | 90 | 25 | 6 |

The data in Table 8 demonstrate that the photoacid generators within the scope of the invention perform well despite a lower sensitivity than the existing photoacid generators and that the inventive resist compositions are improved in exposure latitude over those compositions comprising the existing photoacid generators.

Examples 67 to 84 and Comparative Example 13 to 18

Evaluation of EB Imaging

Using a coater/developer system Clean Track ACT-M (Tokyo Electron Ltd.), each of the positive resist compositions (R-25 to 42 and R-104 to 109) was spin-coated onto a 152-mm square mask blank having a chromium oxynitride film at the outermost surface and pre-baked on a hot plate at 100° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB mask writer system EBM-5000Plus (NuFlare Technology Inc., accelerating voltage 50 keV), then baked (PEB) at 100° C. for 600 seconds, and developed with a 2.38 wt % tetramethylammonium hydroxide aqueous solution, thereby yielding positive patterns.

The patterned blank was observed under a top-down scanning electron microscope (TDSEM). The optimum exposure (Eop) was defined as the exposure dose ($\mu C/cm^2$) which provided a 1:1 resolution at the top and bottom of a 100-nm 1:1 line-and-space pattern. The maximum resolution of the resist was defined as the minimum line width of a line-and-space pattern that could be resolved and separated at the optimum exposure. The 100-nm line-and-space pattern was measured for line edge roughness (LER) under SEM. On observation in cross section of the resist pattern under SEM, it was visually judged whether or not the pattern profile was rectangular. The post-exposure delay (PED) in vacuum was evaluated by exposing imagewise the coated blank on the EB lithography system, holding it in the vacuum system for 24 hours, thereafter effecting PEB and development. The line width of a 100-nm line-and-space pattern at Eop was measured and compared with that of the resist pattern which was baked immediately after exposure, with a difference ($\Delta$CD in nm) being reported. The test results are shown in Table 9.

It is evident from Table 9 that when processed by EB lithography, the resist compositions of the invention are improved in resolution, despite a lower sensitivity, over those compositions comprising the existing photoacid generators. The inventive resist compositions show small values of LER. The profile is kept rectangular without a top loss. The PED in vacuum is stable, indicating that the acid generated upon exposure to high-energy radiation is low diffusible. When a resist composition having a high sensitivity is desired, it may be prepared by adjusting the amount of quencher. Then the chemically amplified resist composition is suited as a fine pattern-forming material adapted for the high-energy radiation lithography for the fabrication of VLSI, and a mask pattern-forming material.

The resist composition comprising the inventive photoacid generator has the advantages of low diffusion and high resolution, despite a lower sensitivity than the existing photoacid generators. Since substantially no volatile decomposition products are formed upon exposure to high-energy radiation, the resist composition comprising the inventive photoacid generator has the advantage of minimized outgassing, as compared with the existing photoacid generators, even when processed by the EUV lithography in high vacuum.

Japanese Patent Application No. 2009-161322 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

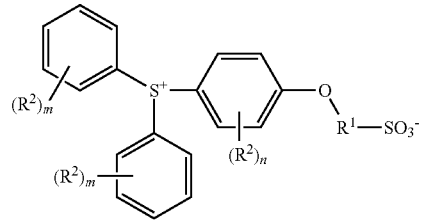

(1)

TABLE 9

| | | Resist composition | Eop ($\mu C/cm^2$) | Maximum resolution (nm) | LER (nm) | PED (nm) | Pattern profile |
|---|---|---|---|---|---|---|---|
| Example | 67 | R-25 | 36 | 45 | 4.1 | 3.4 | Rectangular |
| | 68 | R-26 | 36 | 45 | 4.2 | 3.7 | Rectangular |
| | 69 | R-27 | 35 | 45 | 4.0 | 3.5 | Rectangular |
| | 70 | R-28 | 35 | 45 | 4.1 | 3.7 | Rectangular |
| | 71 | R-29 | 33 | 45 | 4.2 | 3.8 | Rectangular |
| | 72 | R-30 | 33 | 45 | 4.2 | 3.8 | Rectangular |
| | 73 | R-31 | 35 | 45 | 4.3 | 3.6 | Rectangular |
| | 74 | R-32 | 36 | 50 | 4.6 | 3.5 | Slightly rounded top |
| | 75 | R-33 | 37 | 50 | 4.4 | 3.5 | Slightly bulged top |
| | 76 | R-34 | 37 | 50 | 4.5 | 3.4 | Slightly bulged top |
| | 77 | R-35 | 33 | 45 | 4.0 | 3.4 | Rectangular |
| | 78 | R-36 | 33 | 45 | 4.1 | 3.5 | Rectangular |
| | 79 | R-37 | 33 | 45 | 4.0 | 3.6 | Rectangular |
| | 80 | R-38 | 30 | 40 | 3.7 | 3.5 | Rectangular |
| | 81 | R-39 | 30 | 40 | 3.6 | 3.4 | Rectangular |
| | 82 | R-40 | 31 | 45 | 3.9 | 3.5 | Rectangular |
| | 83 | R-41 | 30 | 40 | 3.8 | 3.6 | Rectangular |
| | 84 | R-42 | 33 | 40 | 3.9 | 3.6 | Rectangular |
| Comparative Example | 13 | R-104 | 23 | 65 | 5.8 | 5.2 | Rounded top + footing |
| | 14 | R-105 | 23 | 65 | 5.7 | 5.5 | Rounded top |
| | 15 | R-106 | 22 | 65 | 5.7 | 5.6 | Rounded top + footing |
| | 16 | R-107 | 22 | 65 | 5.6 | 5.8 | Rounded top + footing |
| | 17 | R-108 | 20 | 60 | 5.6 | 5.7 | Rounded top + footing |
| | 18 | R-109 | 21 | 60 | 5.7 | 5.8 | Rounded top + footing | wherein $R^1$ is a $C_1$-$C_{10}$ alkylene or $C_6$-$C_{10}$ arylene group which may be substituted with fluorine or another heteroatom, $R^2$ is each independently methyl, tert-butyl, methoxy or tert-butoxy, or a linking group in the form of oxygen, methylene or sulfone or a direct bond between different benzene rings, m is an integer of 0 to 5, and n is an integer of 0 to 4.

2. A sulfonium salt having the general formula (2):

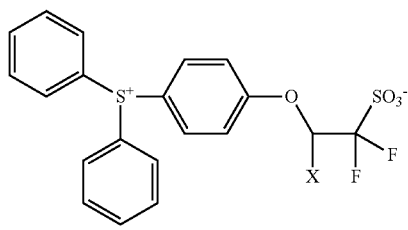

(2)

wherein X is hydrogen or trifluoromethyl.

3. A chemically amplified resist composition comprising the sulfonium salt of claim 1.

4. A chemically amplified positive resist composition comprising the sulfonium salt of claim 1.

5. A pattern forming process comprising the steps of:
applying the resist composition of claim 3 onto a substrate to form a coating,
heat treating the coating and exposing it to high-energy radiation through a photomask,
optionally heat treating the exposed coating and developing it with a developer.

6. A pattern forming process comprising the steps of:
applying the resist composition of claim 3 onto a substrate to form a resist coating,
heat treating the resist coating,
applying onto the resist coating a protective film which is insoluble in water and soluble in an alkaline developer,
exposing the coated substrate to high-energy radiation from a projection lens through a photomask while holding water between the substrate and the projection lens,
optionally heat treating the exposed coating and developing it with a developer.

7. A pattern forming process comprising the steps of applying the positive resist composition of claim 3 onto a substrate to form a coating, heat treating the coating, imagewise writing with an electron beam, optionally heat treating the coating, and developing it with a developer.

8. A pattern forming process comprising the steps of applying the positive resist composition of claim 3 onto a substrate to form a coating, heat treating the coating, exposing the coating to soft x-ray having a wavelength of 3 to 15 nm, optionally heat treating the coating, and developing it with a developer.

* * * * *